US011066571B2

(12) United States Patent
Morita et al.

(10) Patent No.: US 11,066,571 B2
(45) Date of Patent: Jul. 20, 2021

(54) PATTERN FORMING METHOD, UNDER COATING AGENT, AND LAMINATE

(71) Applicant: Oji Holdings Corporation, Tokyo (JP)

(72) Inventors: Kazuyo Morita, Tokyo (JP); Kimiko Hattori, Tokyo (JP)

(73) Assignee: OJI HOLDINGS CORPORATION, Tokyo (JP)

( * ) Notice: Subject to any disclaimer, the term of this patent is extended or adjusted under 35 U.S.C. 154(b) by 98 days.

(21) Appl. No.: 16/344,416

(22) PCT Filed: May 30, 2017

(86) PCT No.: PCT/JP2017/020103
§ 371 (c)(1),
(2) Date: Apr. 24, 2019

(87) PCT Pub. No.: WO2018/078929
PCT Pub. Date: May 3, 2018

(65) Prior Publication Data
US 2020/0048491 A1 Feb. 13, 2020

(30) Foreign Application Priority Data
Oct. 28, 2016 (JP) .............................. JP2016-212352

(51) Int. Cl.
| C09D 133/14 | (2006.01) |
| B05D 1/36 | (2006.01) |
| B05D 7/24 | (2006.01) |
| C07H 7/04 | (2006.01) |
| C07H 13/04 | (2006.01) |
| C08F 212/14 | (2006.01) |
| C08F 220/68 | (2006.01) |
| C09D 153/00 | (2006.01) |
| C08F 290/10 | (2006.01) |
| C08F 297/02 | (2006.01) |
| C07H 13/12 | (2006.01) |
| H01L 21/027 | (2006.01) |

(52) U.S. Cl.
CPC ............. *C09D 133/14* (2013.01); *B05D 1/36* (2013.01); *B05D 7/24* (2013.01); *C07H 7/04* (2013.01); *C07H 13/04* (2013.01); *C07H 13/12* (2013.01); *C08F 212/14* (2013.01); *C08F 220/68* (2013.01); *C08F 290/10* (2013.01); *C08F 297/026* (2013.01); *C09D 153/00* (2013.01); *H01L 21/0271* (2013.01)

(58) Field of Classification Search
CPC ... B05D 1/36; B05D 7/24; C07H 7/04; C07H 13/04; C07H 13/12; C08F 212/14; C08F 220/68; C08F 290/10; C08F 297/026
USPC ...................................................... 427/258
See application file for complete search history.

(56) References Cited

U.S. PATENT DOCUMENTS

| 8,431,611 B2 | 4/2013 | Brando et al. | |
| 2011/0123636 A1* | 5/2011 | Stayton | A61P 37/00 424/497 |
| 2012/0088188 A1* | 4/2012 | Trefonas | B81C 1/00031 430/270.1 |
| 2013/0022785 A1* | 1/2013 | Ellison | C08B 37/0006 428/141 |
| 2016/0194524 A1* | 7/2016 | Yamano | C08F 212/08 427/331 |

FOREIGN PATENT DOCUMENTS

| CN | 1159390 A | 9/1997 |
| CN | 103946254 A | 7/2014 |
| CN | 109153759 A | 1/2019 |
| EP | 3395859 A | 10/2018 |
| EP | 3459981 | 3/2019 |
| JP | H10292147 A | 11/1998 |
| JP | 2004-124088 A | 4/2004 |
| JP | 2010-91630 A | 4/2010 |
| JP | 2010091630 A * | 4/2010 |
| JP | 2012-62365 A | 3/2012 |
| JP | 2014-5325 A | 1/2014 |
| JP | 2014-47269 A | 3/2014 |
| JP | 2014-185311 A | 10/2014 |

(Continued)

OTHER PUBLICATIONS

Extended European Search Report dated Jun. 17, 2020 issued in the corresponding European Patent Application No. 17866205.2.
Zi-Chen Li et al., Macromolecular Rapid Communications, vol. 21, No. 7, Apr. 1, 2000, pp. 375-380, XP55612142.
Wouter M. J. Kloosterman et al., Chemistry—An Asian Journal, vol. 9, No. 8, Aug. 27, 2014, pp. 2156-2161, XP55239374.
Kishimoto et al., The Japan Wood Research Society, Jan. 1, 2002, pp. 32-37, XP55701721.

(Continued)

*Primary Examiner* — Michael Bernshteyn
(74) *Attorney, Agent, or Firm* — Browdy and Neimark, PLLC

(57) ABSTRACT

It is an object of the present invention to provide a pattern forming method capable of easily forming a phase-separated structure with high accuracy, even in the case of widening the applicable range of a pattern size. The present invention relates to a pattern forming method comprising: applying an under coating agent onto a substrate, and applying a self-assembly composition for pattern formation to the surface of the substrate, onto which the under coating agent has been applied, and then forming a self-assembly film according to self-assembly phase separation, wherein the self-assembly composition for pattern formation comprises a block copolymer comprising a polymerization unit (a) having at least one selected from a structure represented by a formula (103) and a structure represented by a formula (104), and a polymerization unit (b) having a structure represented by a formula (105).

6 Claims, 4 Drawing Sheets

(56) References Cited

FOREIGN PATENT DOCUMENTS

| | | | |
|---|---|---|---|
| JP | 2014185311 A | * | 10/2014 |
| JP | 2016-79242 A | | 5/2016 |
| JP | 2016-107206 A | | 6/2016 |
| JP | 2016-108435 A | | 6/2016 |
| TW | 201428046 A | | 7/2014 |
| WO | 2009/140429 A1 | | 11/2009 |
| WO | 2012/013911 A1 | | 2/2012 |
| WO | 2012/177839 A1 | | 12/2012 |
| WO | 2014/162872 A1 | | 10/2014 |
| WO | 2017/110190 A1 | | 6/2017 |

OTHER PUBLICATIONS

Karin Thorsheim et al., Glycoconjugate Journal, Chapman & Hall, Boston, vol. 33, No. 2, Mar. 29, 2016, pp. 245-257, XP35909604.

International Preliminary Report on Patentability of Chapter I for corresponding PCT International Application No. PCT/JP2017/020103, dated May 9, 2019, with English translation.

International Search Report and Written Opinion for corresponding PCT International Application No. PCT/JP2017/020103.

Toshiba Review vol. 67, No. 4, 2012, pp. 44-47 with its English translation.

Ting, S. R. Simon et. al. Lectin Recognizable Biomaterials Synthesized via Nitroxide-Mediated Polymerization of a Methacryloyl Galactose Monomer, Macromolecules, 2009, vol. 42, No. 24, p. 9422-9434.

Ke, Bei-Bei, et. al. Controllable Construction of Carbohydrate Microarrays by Site-Directed Grafting on Self-Organized Porous Films, Langmuir, 2010, vol. 26, No. 11, p. 8946-8952.

Office Action dated May 7, 2021 issued in the corresponding Chinese patent application No. 201780066048.4 with its English Machine Translation.

Atsushi Narumi et al., Synthesis of amphiphilic triblock copolymer of polystyrene and poly (4-vinylbenzyl glucoside) via TEMPO-mediated living radical polymerization, Polymer, Aug. 31, 2002, pp. 4835-4840 (2002).

Atsushi Narumi et al., Glycoconjugated Polymer: Synthesis and Characterization of Poly (vinyl saccharide)-block-Polystyrene-block-Poly(vinyl saccharide) as an Amphiphilic ABA Triblock Copolymer, Journal of Polymer Science: Part A: Polymer Chemistry, Jul. 1, 2006, pp. 3978-3985 (2006).

* cited by examiner

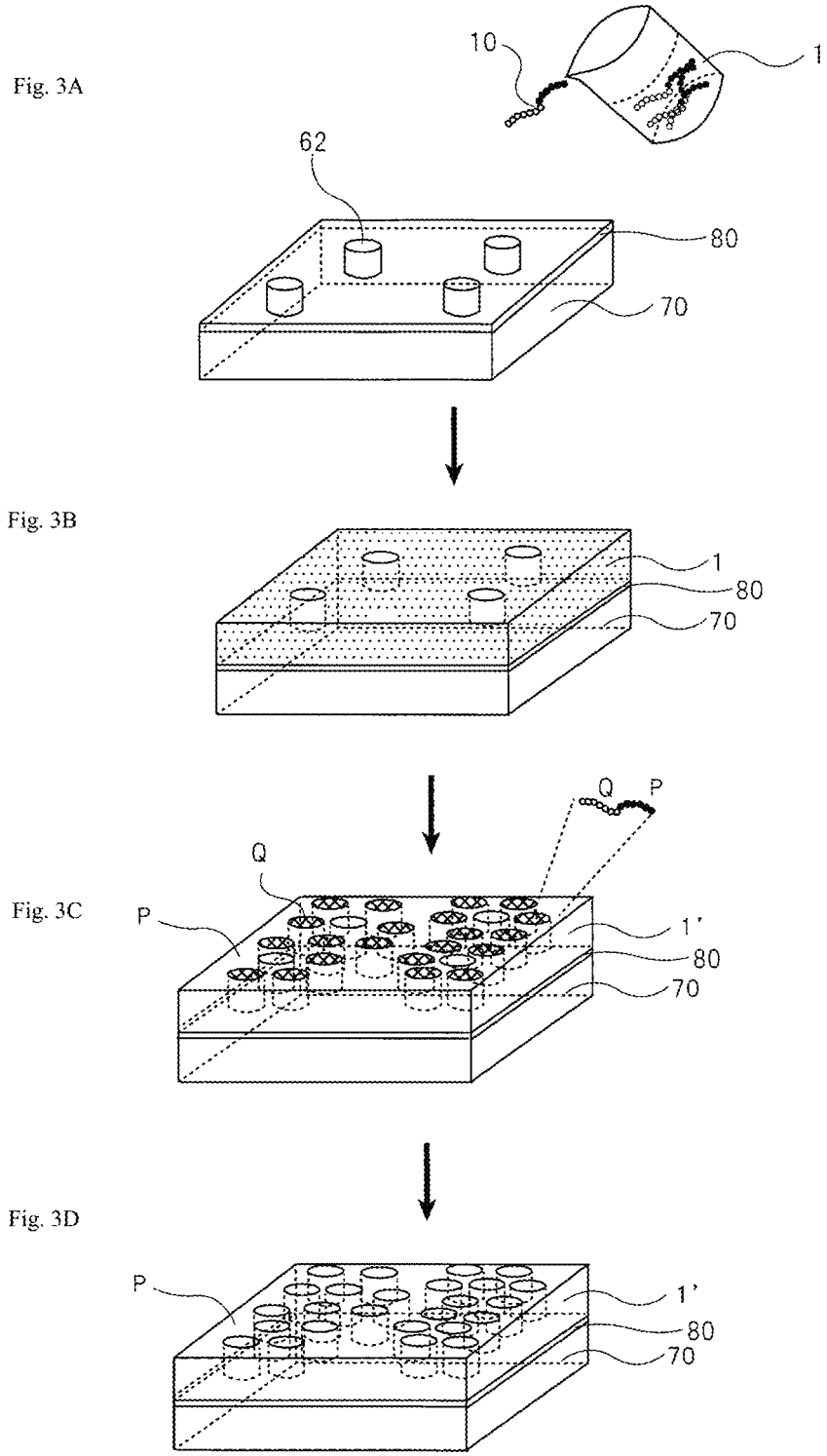

PATTERN FORMING METHOD, UNDER COATING AGENT, AND LAMINATE

TECHNICAL FIELD

The present invention relates to a pattern forming method, an under coating agent, and a laminate.

BACKGROUND ART

Electronic devices such as semiconductors have been required to be highly integrated as a result of miniaturization thereof. With regard to the patterns of semiconductors, miniaturization and the diversification of the shapes have been studied. As such pattern forming methods, a double patterning method, a lithography method using electron beam, and a pattern forming method involving self-assembly using a directed self-assembly material (hereafter also referred to as a "self-assembly composition for pattern formation") have been known.

Since the self-assembly composition for pattern formation undergoes phase separation for self-assembly, it does not need an expensive electron beam drawing device and does not cause complicated patterning processes found in the double patterning method. Accordingly, the self-assembly composition for pattern formation is advantageous in terms of costs. As such self-assembly compositions for pattern formation, for example, diblock copolymers such as polystyrene-polymethyl methacrylate (PS-PMMA) have been known (for example, Non-Patent Document 1). In Non-Patent Document 1, PS-PMMA is applied onto a guide pattern, and is then heated to form a phase-separated structure. Thereafter, an etching step is performed, so that a region consisting of a polymerization unit on one side of the diblock copolymer is removed, thereby forming a fine pattern.

As such a self-assembly composition for pattern formation, the use of a material other than PS-PMMA has also been studied. For example, Patent Document 1 discloses a self-assembly composition for pattern formation, which comprises, as a main chain, a styrene-based polymer, an acryl-based polymer or the like, and has a group containing a heteroatom at the terminus thereof. In Patent Document 1, formation of a sufficiently fine pattern by using a self-assembly composition for pattern formation as described above has been studied.

In order to form a fine pattern, there has also been proposed a method comprising applying an under coating agent onto a substrate to form an under layer, and then forming a pattern on the under layer. For example, Patent Documents 2 and 3 disclose an under coating agent used for the phase separation of a layer comprising a block copolymer formed by binding a polymer containing styrene or a derivative thereof as a constitutional unit with a polymer containing (meth)acrylic acid ester as a constitutional unit. Patent Document 3 describes that an under layer is established, so that the adhesiveness between a substrate and an layer containing a block copolymer formed on the substrate can be enhanced, thereby forming a fine pattern.

PRIOR ART DOCUMENTS

Patent Documents

Patent Document 1: JP-A-2014-5325
Patent Document 2: JP-A-2012-62365
Patent Document 3: JP-A-2016-107206

Non-Patent Documents

Non-Patent Document 1: Toshiba Review Vol. 67, No. 4, 2012, pp. 44-47

SUMMARY OF INVENTION

Object to be Solved by the Invention

PS-PMMA has been frequently used as a self-assembly composition that forms a pattern by phase separation. Although PS-PMMA is a material capable of highly accurately forming a pattern in a range from approximately 15 nm to 30 nm, by a combination with an under layer, the PS-PMMA has been problematic in that it is difficult to form a pattern out of the aforementioned range.

Moreover, as a result of studies conducted by the present inventors, it has been elucidated that, even in the case of using a self-assembly composition for pattern formation as described in Patent Document 1, when the applicable range of a pattern size is narrow, and thus, in particular, when a pattern with a size of 30 nm or more is to be formed, a favorable phase-separated structure cannot be formed.

Hence, in order to overcome the aforementioned problems of the prior art techniques, the present inventors have further conducted studies for the purpose of providing a pattern forming method capable of easily forming a phase-separated structure with high accuracy, even in the case of widening the applicable range of a pattern size.

Means for Solving the Object

As a result of intensive studies conducted directed towards achieving the aforementioned object, the present inventors have found that, when a pattern is formed using a self-assembly composition for pattern formation, a under coating agent is applied onto a substrate, and then, a self-assembly composition for pattern formation comprising a block copolymer having at least two types of polymerization units having predetermined structures is applied onto the substrate, so that a phase-separated structure can be easily formed with good accuracy.

Specifically, the present invention has the following configurations.

[1] A pattern forming method comprising:
  applying an under coating agent onto a substrate, and
  applying a self-assembly composition for pattern formation to the surface of the substrate, onto which the under coating agent has been applied, and then forming a self-assembly film according to self-assembly phase separation, wherein
  the self-assembly composition for pattern formation comprises a block copolymer comprising a polymerization unit (a) having at least one selected from a structure represented by the following formula (103) and a structure represented by the following formula (104), and a polymerization unit (b) having a structure represented by the following formula (105), and the content rate of a sugar moiety in the block copolymer is 3% by mass or more and 80% b mass or less, based on the total mass of the block copolymer:

[Formula 1]

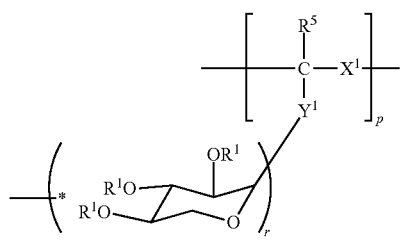

Formula (103)

[Formula 2]

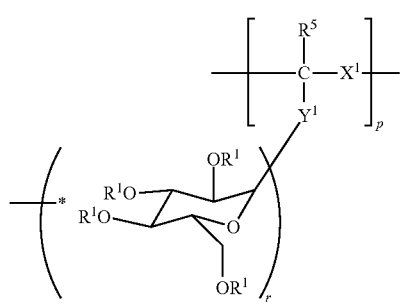

Formula (104)

[Formula 3]

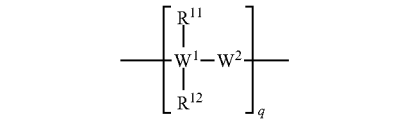

Formula (105)

wherein, in the formulae (103) and (104), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another, R represents a hydrogen atom or an alkyl group, and a plurality of $R^5$ may be identical to or different from one another; $X^1$ and $Y^1$ each independently represent a single bond or a linking group, a plurality of $X^1$ may be identical to or different from one another, and a plurality of $Y^1$ may be identical to or different from one another; p represents an integer of 2 or more and 3000 or less, r represents an integer of 0 or more, and at least one of a plurality of r represents an integer of 1 or more; and the symbol * represents a binding site with any one of $R^1$, or a binding site with any one oxygen atom to which $R^1$ binds, instead of $R^1$, when r represents 2 or more, or represents a binding site with any one oxygen atom to which $R^1$ binds, instead of $R^1$; and in the formula (105), $W^1$ represents a carbon atom or a silicon atom, and a plurality of $W^1$ may be identical to or different from one another, $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another; $R^{11}$ represents a hydrogen atom, a methyl group, or a hydroxyl group, and a plurality of $R^{11}$ may be identical to or different from one another; $R^{12}$ represents a hydrogen atom, a hydroxyl group, an acetyl group, a methoxycarbonyl group, an aryl group, or a pyridyl group, and a plurality of $R^{12}$ may be identical to or different from one another, and q represents an integer of 2 or more and 3000 or less.

[2] The pattern forming method according to [1], wherein the under coating agent comprises a polymer containing at least one selected from a (meth)acrylate-derived unit optionally having a substituent and a styrene-derived unit optionally having a substituent.

[3] The pattern forming method according to [1] or [2], wherein the under coating agent comprises a polymer containing at least one selected from structures represented by the following formulae (203) to (206):

[Formula 4]

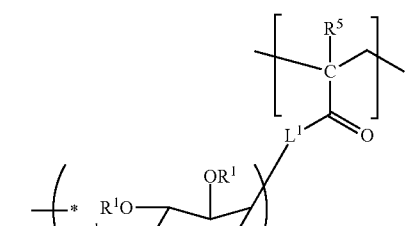

Formula (203)

[Formula 5]

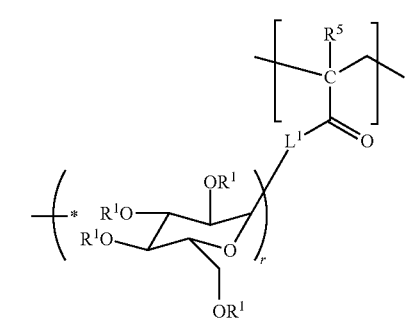

Formula (204)

[Formula 6]

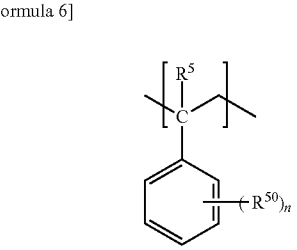

Formula (205)

[Formula 7]

Formula (206)

wherein, in the formulae (203) and (204), $L^1$ represents —O—, —S—, —NH—, —O—$(CH_2)_n$—O—, or —O—$(CH_2)_n$—N—(C=O)—N—, provided that n represents an integer of 1 or more and 10 or less; $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another, $R^5$ represents a hydrogen atom or an alkyl group; r represents an integer of 1 or more, and the symbol * represents a binding site with any one of $R^1$, or a binding site with any one oxygen atom to which $R^1$ binds, instead of $R^1$, when r represents 2 or more;

in the formula (205), $R^5$ represents a hydrogen atom or an alkyl group, $R^{50}$ represents an organic group or a hydroxyl group, and n represents an integer of 0 to 5; and in the formula (206), $R^5$ represents a hydrogen atom or an alkyl group, and $R^{60}$ represents an alkyl group.

[4] The pattern forming method according to any one of [1] to [3], which further comprises an etching step, after completion of the forming the self-assembly film.

[5] The pattern forming method according to [4], wherein the etching step is a dry etching step.

[6] The pattern forming method according to [4], wherein the etching step is a wet etching step.

[7] A under coating agent used for phase separation of a self-assembly composition for pattern formation, wherein the under coating agent comprises a polymer containing at least one selected from a (meth)acrylate-derived unit optionally having a substituent and a styrene-derived unit optionally having a substituent, the self-assembly composition for pattern formation comprises a block copolymer comprising a polymerization unit (a) having at least one selected from a structure represented by the following formula (103) and a structure represented by the following formula (104), and a polymerization unit (b) having a structure represented by the following formula (105), and the content rate of a sugar moiety in the block copolymer is 3% by mass or more and 80% by mass or less, based on the total mass of the block copolymer:

[Formula 8]

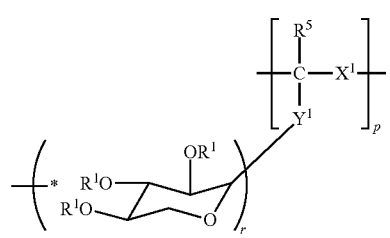

Formula (103)

[Formula 9]

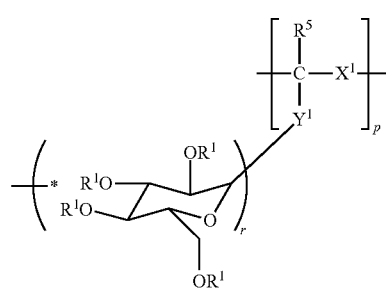

Formula (104)

[Formula 10]

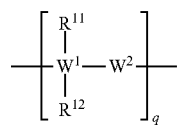

Formula (105)

wherein, in the formulae (103) and (104), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another, R represents a hydrogen atom or an alkyl group, and a plurality of $R^5$ may be identical to or different from one another; $X^1$ and $Y^1$ each independently represent a single bond or a linking group, a plurality of $X^1$ may be identical to or different from one another, and a plurality of $Y^1$ may be identical to or different from one another; p represents an integer of 2 or more and 3000 or less, r represents an integer of 0 or more, and at least one of a plurality of r represents an integer of 1 or more; and the symbol * represents a binding site with any one of $R^1$, or a binding site with any one oxygen atom to which $R^1$ binds, instead of $R^1$, when r represents 2 or more, or represents a binding site with any one oxygen atom to which $R^1$ binds, instead of $R^1$; and in the formula (105), $W^1$ represents a carbon atom or a silicon atom, and a plurality of $W^1$ may be identical to or different from one another, $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another; $R^{11}$ represents a hydrogen atom, a methyl group, or a hydroxyl group, and a plurality of $R^{11}$ may be identical to or different from one another; $R^{12}$ represents a hydrogen atom, a hydroxyl group, an acetyl group, a methoxycarbonyl group, an aryl group, or a pyridyl group, and a plurality of $R^{12}$ may be identical to or different from one another, and q represents an integer of 2 or more and 3000 or less.

[8] The under coating agent according to [7], which comprises a polymer containing at least one selected from structures represented by the following formulae (203) to (206):

[Formula 11]

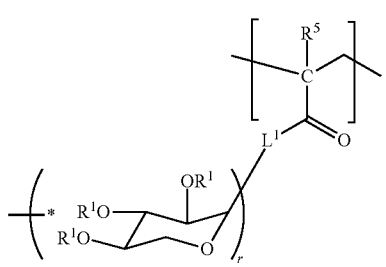

Formula (203)

[Formula 12]

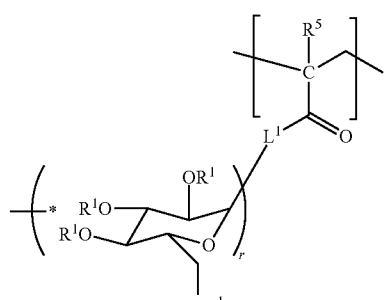

Formula (204)

[Formula 13]

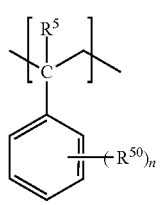

Formula (205)

[Formula 14]

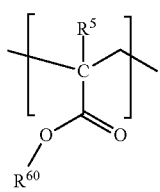

Formula (206)

[Formula 15]

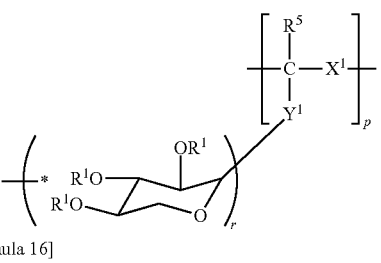

Formula (103)

[Formula 16]

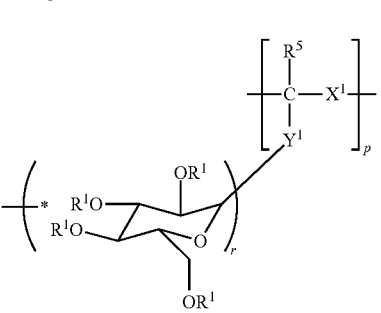

Formula (104)

[Formula 17]

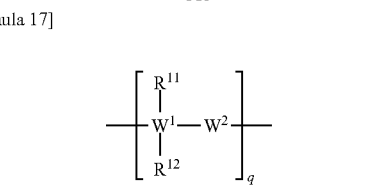

Formula (105)

wherein, in the formulae (203) and (204), $L^1$ represents —O—, —S—, —NH—, —O—$(CH_2)_n$—O—, or —O—$(CH_2)_n$—N—(C=O)—N—, provided that n represents an integer of 1 or more and 10 or less; $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another, $R^5$ represents a hydrogen atom or an alkyl group; r represents an integer of 1 or more, and the symbol * represents a binding site with any one of $R^1$, or a binding site with any one oxygen atom to which $R^1$ binds, instead of $R^1$, when r represents 2 or more;

in the formula (205), $R^5$ represents a hydrogen atom or an alkyl group, $R^{50}$ represents an organic group or a hydroxyl group, and n represents an integer of 0 to 5; and in the formula (206), $R^5$ represents a hydrogen atom or an alkyl group, and $R^{60}$ represents an alkyl group.

[9] A laminate having a substrate, an under layer, and a pattern-forming layer in this order, wherein the under layer comprises a polymer containing at least one selected from a (meth)acrylate-derived unit optionally having a substituent and a styrene-derived unit optionally having a substituent, the pattern-forming layer comprises a block copolymer comprising a polymerization unit (a) having at least one selected from a structure represented by the following formula (103) and a structure represented by the following formula (104), and a polymerization unit (b) having a structure represented by the following formula (105), and the content rate of a sugar moiety in the block copolymer is 3% by mass or more and 80% by mass or less, based on the total mass of the block copolymer wherein, in the formulae (103) and (104), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another, $R^5$ represents a hydrogen atom or an alkyl group, and a plurality of $R^5$ may be identical to or different from one another; $X^1$ and $Y^1$ each independently represent a single bond or a linking group, a plurality of $X^1$ may be identical to or different from one another, and a plurality of $Y^1$ may be identical to or different from one another; p represents an integer of 2 or more and 3000 or less, r represents an integer of 0 or more, and at least one of a plurality of r represents an integer of 1 or more; and the symbol * represents a binding site with any one of $R^1$, or a binding site with any one oxygen atom to which $R^1$ binds, instead of $R^1$, when r represents 2 or more; and in the formula (105), $W^1$ represents a carbon atom or a silicon atom, and a plurality of $W^1$ may be identical to or different from one another, $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another; $R^{11}$ represents a hydrogen atom, a methyl group, or a hydroxyl group, and a plurality of $R^{11}$ may be identical to or different from one another; $R^{12}$ represents a hydrogen atom, a hydroxyl group, an acetyl group, a methoxycarbonyl group, an aryl group, or a pyridyl group, and a plurality of $R^{12}$ may be identical to or different from one another, and q represents an integer of 2 or more and 3000 or less.

[10] The laminate according to [9], wherein the under layer comprises a polymer containing at least one selected from structures represented by the following formulae (203) to (206):

[Formula 18]

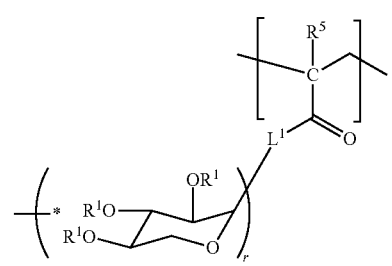

Formula (203)

[Formula 19]

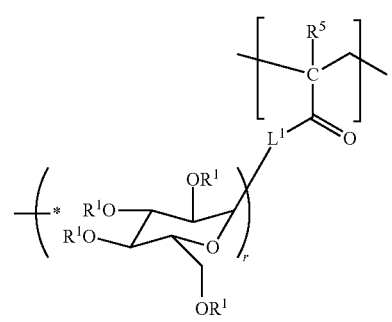

Formula (204)

[Formula 20]

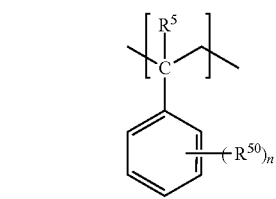

Formula (205)

[Formula 21]

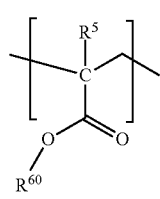

Formula (206)

wherein, in the formulae (203) and (204), $L^1$ represents —O—, —S—, —NH—, —O—$(CH_2)_n$—O—, or —O—$(CH_2)_n$—N—(C=O)—N—, provided that n represents an integer of 1 or more and 10 or less; $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another, $R^5$ represents a hydrogen atom or an alkyl group; r represents an integer of 1 or more, and the symbol * represents a binding site with any one of $R^1$, or a binding site with any one oxygen atom to which $R^1$ binds, instead of $R^1$, when r represents 2 or more;

in the formula (205), $R^5$ represents a hydrogen atom or an alkyl group, $R^{50}$ represents an organic group or a hydroxyl group, and n represents an integer of 0 to 5; and in the formula (206), $R^5$ represents a hydrogen atom or an alkyl group, and $R^{60}$ represents an alkyl group.

Advantageous Effects of Invention

According to the present invention, by using a self-assembly composition for pattern formation, a phase-separated structure, in which the applicable range of a pattern size is widened, can be easily formed with high accuracy.

BRIEF DESCRIPTION OF DRAWINGS

FIGS. 3A-3D are schematic views showing a pattern-forming step.

EMBODIMENTS OF CARRYING OUT THE INVENTION

Figure 1A:
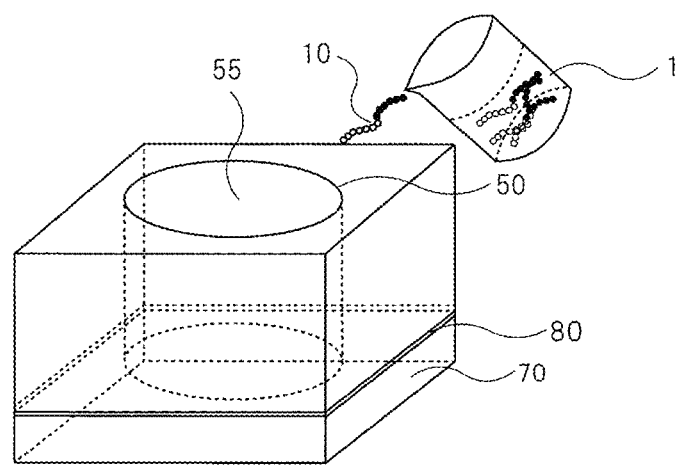
FIGS. 1A-1C are schematic views showing a pattern-forming step.

Hereinafter, the present invention will be described in detail. The below-mentioned constituent features will be explained based on representative embodiments or specific examples in some cases. However, the present invention is not limited to such embodiments. It is to be noted that substituents, regarding which substitution and/or non-substitution are not explicitly mentioned, are understood that they may optionally have any given substituents. In addition, in the present description, "(meth)acrylate" is meant to include both "acrylate" and "methacrylate."

(Self-Assembly Composition for Pattern Formation)

The present invention relates to a pattern forming method comprising: a step of applying an under coating agent onto a substrate, and a step of applying a self-assembly composition for pattern formation to the surface of the substrate, onto which the under coating agent has been applied, and then forming a self-assembly film according to self-assembly phase separation. The self-assembly composition for pattern formation used in the present invention comprises a block copolymer comprising a polymerization unit (a) having at least one selected from a structure represented by the following formula (103) and a structure represented by the following formula (104), and a polymerization unit (b) having a structure represented by the following formula (105). Moreover, the content rate of a sugar moiety in the block copolymer is 3% by mass or more and 80% by mass or less, based on the total mass of the block copolymer.

[Formula 22]

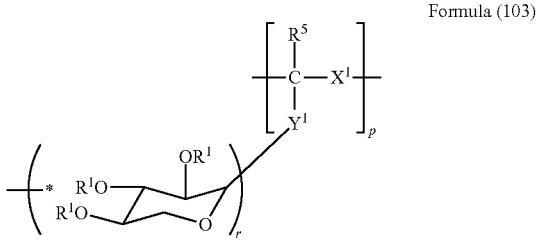

Formula (103)

[Formula 23]

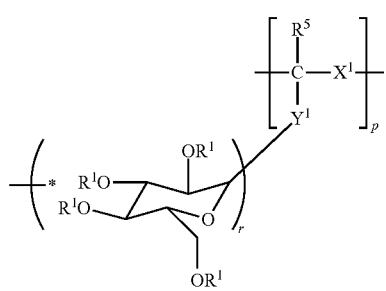

Formula (104)

[Formula 24]

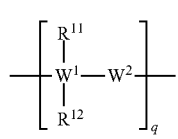

Formula (105)

In the above formulae (103) and (104), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another. $R^5$ represents a hydrogen atom or an alkyl group, and a plurality of $R^5$ may be identical to or different from one another. $X^1$ and $Y^1$ each independently represent a single bond or a linking group, a plurality of $X^1$ may be identical to or different from one another, and a plurality of $Y^1$ may be identical to or different from one another. p represents an integer of 2 or more and 3000 or less, r represents an integer of 0 or more, and at least one of a plurality of r represents an integer of 1 or more. The symbol * represents a binding site with any one of $R^1$, or a binding site with any one oxygen atom to which $R^1$ binds, instead of $R^1$, when r represents 2 or more.

In the above formula (105), $W^1$ represents a carbon atom or a silicon atom, and a plurality of $W^1$ may be identical to or different from one another. $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another. $R^{11}$ represents a hydrogen atom, a methyl group, or a hydroxyl group, and a plurality of $R^{11}$ may be identical to or different from one another. $R^{12}$ represents a hydrogen atom, a hydroxyl group, an acetyl group, a methoxycarbonyl group, an aryl group, or a pyridyl group, and a plurality of $R^{12}$ may be identical to or different from one another. q represents an integer of 2 or more and 3000 or less.

The term "self-assembly (Directed self-assembly)" is used in the present description to mean a phenomenon, which is not caused by only control by external factors, but spontaneously constructs formation or structures. In the present invention, a self-assembly composition for pattern formation is applied onto, for example, a substrate, and annealing and the like are then carried out, so that a film having a phase-separated structure (a self-assembly film) can be formed by self-assembling, and thereafter, a part of phase is removed from this self-assembly film, so that a pattern can be formed.

The self-assembly composition for pattern formation has the above-described structure, and thus, the introduction rate of a sugar moiety (sugar chain) and the introduction rate of the polymerization unit (a) in the block copolymer can be enhanced. Thereby, the cohesiveness of each polymerization unit can be enhanced. If the cohesiveness of each polymerization unit is high, the phase separation ability of the block copolymer is increased, and the applicable range of a pattern size can also be widened. Moreover, since it becomes easy to control the polymerization degree of the block copolymer in the self-assembly composition for pattern formation, even in a case where a large-size pattern is to be formed, a favorable phase-separated structure can be formed. Furthermore, when the self-assembly composition for pattern formation is used, even in a case where a fine pattern structure with a size of, for example, 10 nm or less is to be formed, the pattern can be easily formed with high accuracy.

In the present invention, since there is a large difference in terms of hydrophilicity (hydrophobicity) between the polymerization unit (a) and the polymerization unit (b) and further, the cohesiveness of each polymerization unit is high, phase separation performance is high. Specifically, since the polymerization unit (a) has high hydrophilicity and the polymerization unit (b) has high hydrophobicity, all sizes of patterns can be formed. In addition, in the present invention, the cohesiveness of each polymerization unit can be enhanced by setting the introduction rate of a sugar chain capable of exhibiting the hydrophilicity of the polymerization unit (a) within a suitable range, and as a result, a better phase-separated structure can be easily formed. As such, the self-assembly composition for pattern formation is a material suitable for formation of all sizes of patterns. It is to be noted that, in the present description, the size of a pattern is a pitch size corresponding to each component in a phase-separated structure. Specifically, the pitch size of a portion consisting of polymerization units that remain after completion of the etching step is referred to as a pattern size.

The self-assembly composition for pattern formation is also characterized in that it has a large difference in the etching rate after formation of a phase-separated structure. Specifically, the etching rate of a region consisting of the polymerization unit (a) having the structure represented by the formula (103) and/or the formula (104) is high, whereas the etching rate of a region consisting of the polymerization unit (b) having the structure represented by the formula (105) is low, and thus, the etching step can be efficiently carried out. Furthermore, the pattern shape after completion of the etching can be easily processed into a desired shape.

(Block Copolymer)

A block copolymer comprises a polymerization unit (a) and a polymerization unit (b). The polymerization unit (a) has at least one selected from the structure represented by the following formula (103) and the structure represented by the following formula (104), whereas the polymerization unit (b) has the structure represented by the following formula (105). The block copolymer is preferably an A-B type diblock copolymer comprising the polymerization unit (a) and the polymerization unit (b), but it may also be a block copolymer comprising a plurality of polymerization units (a) and a plurality of polymerization units (b).

[Formula 25]

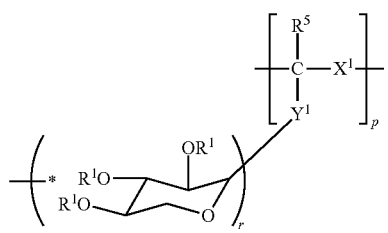

Formula (103)

[Formula 26]

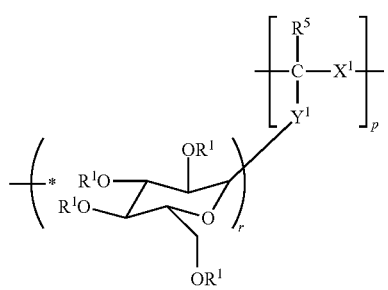

Formula (104)

[Formula 27]

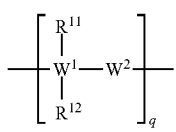

Formula (105)

In the above formulae (103) and (104), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another. $R^5$ represents a hydrogen atom or an alkyl group, and a plurality of $R^5$ may be identical to or different from one another. $X^1$ and $Y^1$ each independently represent a single bond or a linking group, a plurality of $X^1$ may be identical to or different from one another, and a plurality of $Y^1$ may be identical to or different from one another. p represents an integer of 2 or more and 3000 or less, r represents an integer of 0 or more, and at least one of a plurality of r represents an integer of 1 or more. The symbol * represents a binding site with any one of $R^1$, or a binding site with any one oxygen atom to which $R^1$ binds, instead of $R^1$, when r represents 2 or more.

In the above formula (105), $W^1$ represents a carbon atom or a silicon atom, and a plurality of $W^1$ may be identical to or different from one another. $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another. $R^{11}$ represents a hydrogen atom, a methyl group, or a hydroxyl group, and a plurality of $R^{11}$ may be identical to or different from one another. $R^{12}$ represents a hydrogen atom, a hydroxyl group, an acetyl group, a methoxycarbonyl group, an aryl group, or a pyridyl group, and a plurality of $R^{12}$ may be identical to or different from one another. q represents an integer of 2 or more and 3000 or less.

In the formulae (103) and (104), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another. Among others, preferably, $R^1$ each independently represents a hydrogen atom or an acyl group containing 1 or more and 3 or less carbon atoms. Besides, the above-described alkyl group also comprises a sugar chain. That is to say, the sugar chain portion of the polymerization unit (a) may further have a branched chain.

When $R^1$ is an alkyl group or an acyl group, the number of carbon atoms possessed by the group can be selected, as appropriate, depending on purpose. For example, the number of carbon atoms is preferably 2 or more, and is also preferably 200 or less, more preferably 100 or less, further preferably 20 or less, and particularly preferably 4 or less.

Specific examples of $R^1$ include: acyl groups such as an acetyl group, a propanoyl group, a butyryl group, an isobutyryl group, a valeryl group, an isovaleryl group, a pivaloyl group, a hexanoyl group, an octanoyl group, a chloroacetyl group, a trifluoroacetyl group, a cyclopentanecarbonyl group, a cyclohexanecarbonyl group, a benzoyl group, a methoxybenzoyl group, or a chlorobenzoyl group; and alkyl groups such as a methyl group, an ethyl group, a propyl group, a butyl group, or a t-butyl group. Among these examples, an acetyl group, a propanoyl group, a butyryl group, and an isobutyryl group are preferable, and an acetyl group is particularly preferable.

In the formulae (103) and (104), $R^5$ represents a hydrogen atom or an alkyl group, and a plurality of $R^5$ may be identical to or different from one another. Among others, $R^5$ is preferably a hydrogen atom or an alkyl group containing 1 or more and 3 or less carbon atoms, and is particularly preferably a hydrogen atom or a methyl group.

In the formulae (103) and (104), $X^1$ and $Y^1$ each independently represent a single bond or a linking group, and a plurality of $X^1$ may be identical to or different from one another, and a plurality of $Y^1$ may be identical to or different from one another.

When $X^1$ is a linking group, examples of the $X^1$ include an alkylene group, —O—, —$NH_2$—, and a group containing a carbonyl group and the like. $X^1$ is preferably a single bond or an alkylene group containing 1 or more and 6 or less carbon atoms, and is more preferably an alkylene group containing 1 or more and 3 or less carbon atoms.

When $Y^1$ is a linking group, examples of the $Y^1$ include an alkylene group, a phenylene group, —O—, and —C(=O)O—. $Y^1$ may also be a linking group formed by combining these groups. Among others, $Y^1$ is preferably a linking group represented by any of the following structural formulae.

[Formula 28]

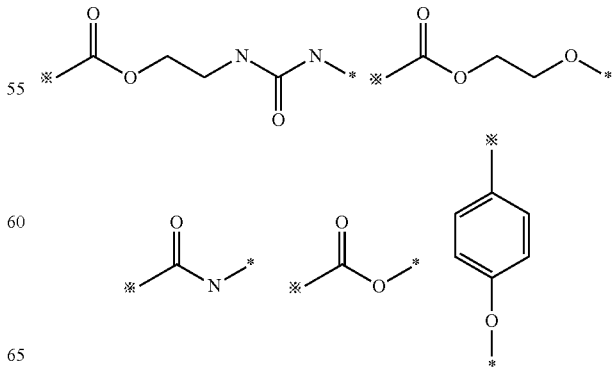

In the above structural formulae, the symbol ⤬ represents a binding site with the main chain side, and the symbol * represents a binding site with the sugar moiety of the side chain.

In the formulae (103) and (104), p may be 2 or more, preferably 3 or more, more preferably 4 or more, and further preferably 5 or more. On the other hand, p may be 3000 or less, preferably 2500 or less, more preferably 2000 or less, and further preferably 1500 or less.

The value of p in the formulae (103) and (104) is preferably calculated from the value measured by gel permeation chromatography. Other measurement methods include size exclusion chromatography, a light scattering method, a viscosity method, an end-group analysis method, and a sedimentation velocity method. The molecular weight is obtained from such a measurement value, and the obtained molecular weight is then divided by the molecular weight of a unit structure to obtain the p value. At this time, the molecular weight of a unit structure can be obtained from the spectra of $^1$H-NMR and $^{13}$C-NMR and the mean value of r. Moreover, it is more preferable to obtain a unit structure, using information regarding MS spectrum, IR spectrum and the like, as well as the information of NMR.

In the formulae (103) and (104), r represents an integer of 0 or more, and at least one of a plurality of r represents an integer of 1 or more. At least one of r is preferably 2 or more, more preferably 3 or more, and further preferably 5 or more. On the other hand, r is preferably 1500 or less, more preferably 1200 or less, further preferably 500 or less, still further preferably 100 or less, particularly preferably 50 or less, and most preferably 10 or less. Among others, r is preferably an integer of 1 or more and 10 or less.

As is clear from the structural formulae, namely, from the formulae (103) and (104), these structures comprise a glucose unit or a xylose unit, namely, a sugar moiety. In the formulae (103) and (104), since p is 2 or more, sugar moieties each having a different polymerization degree may be linked to one another via $Y^1$ in a p number of repeating units. That is, r may be a different value in the p number of individual repeating units, as long as the r is within the above-described range.

The average polymerization degree of a sugar unit is the same as the preferred range of the above-described r. It is to be noted that the polymerization degree of a sugar unit, r, is the number of sugar units that form one sugar moiety, but that since p is 2 or more, the structures represented by the formulae (103) and (104) comprise a plurality of sugar moieties. Hence, the structures represented by the formulae (103) and (104) may comprise sugar moieties having each different polymerization degree r, and thus, the average polymerization degree of sugar units is not necessarily an integer. Moreover, when the sugar moiety has a side chain structure, the number of sugar units constituting the side chain is also included in the average polymerization degree. The average polymerization degree of the above-described sugar unit can be calculated by the following measurement method.

First, a solution containing the polymerization unit (a) is maintained at 50° C., and is centrifuged at 15000 rpm for 15 minutes to remove insoluble matters. Thereafter, the amount of total sugar and the amount of reducing sugar (both relative to xylose) in the supernatant are measured. The amount of total sugar is divided by the amount of reducing sugar to calculate an average polymerization degree. When the above-described measurement method cannot be adopted, gel permeation chromatography, size exclusion chromatography, a light scattering method, a viscosity method, an end-group analysis method, a sedimentation velocity method, a MULDI-TOF-MS method, a structure analysis method involving NMR, etc. may be adopted.

When the average polymerization degree of the sugar unit is measured after the synthesis of a block copolymer, the integrated value of a sugar chain-derived peak (around 3.3-5.5 ppm) and the integrated value of other component-derived peak of the polymerization unit (a) are calculated according to $^1$H-NMR, and the average polymerization degree is then calculated based on the ratio of individual integrated values. In addition, when $R^1$ is not a hydrogen atom in the formulae (103) and (104), the integrated value of an —$OR^1$ group-derived peak can also be used, instead of the integrated value of the sugar chain-derived peak (however, in this case, $R^1$ in the —$OR^1$ group is not a sugar chain).

In the formulae (103) and (104), the symbol * represents a binding site with any one of $R^1$, when r represents 2 or more, or represents a binding site with any one oxygen atom to which $R^1$ binds, instead of $R^1$. That is to say, the polymerization portion of sugar units in the formulae (103) and (104) may be either $R^1$ or an oxygen atom to which $R^1$ binds, and either one portion is preferably the polymerization portion. When $R^1$ is an alkyl group having a substituent, $R^1$ may be a sugar chain. Accordingly, even if there is only one binding site represented by the symbol * in the formulae (103) and (104), the sugar chain actually has a side chain consisting of further sugar chains in some cases.

In the formula (105), $W^1$ represents a carbon atom or a silicon atom, and a plurality of $W^1$ may be identical to or different from one another. Among others, $W^1$ is preferably a carbon atom. Moreover, in the formula (105), $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another. Among others, $W^2$ is preferably —$CR_2$—, and more preferably —$CH_2$—.

In the formula (105), $R^{11}$ represents a hydrogen atom, a methyl group, or a hydroxyl group, and a plurality of $R^{11}$ may be identical to or different from one another. $R^{11}$ is more preferably a hydrogen atom or a methyl group, and further preferably a hydrogen atom. Moreover, in the formula (105), $R^{12}$ represents a hydrogen atom, a hydroxyl group, an acetyl group, a methoxycarbonyl group, an aryl group, or a pyridyl group, and a plurality of $R^{12}$ may be identical to or different from one another. $R^{12}$ is preferably an aryl group or a pyridyl group, more preferably an aryl group, and further preferably a phenyl group. Furthermore, the phenyl group is preferably a phenyl group having a substituent. Examples of such a phenyl group having a substituent include a 4-t-butylphenyl group, a methoxyphenyl group, a dimethoxyphenyl group, a trimethoxyphenyl group, a trimethylsilylphenyl group, and a tetramethyldisilylphenyl group. Also, $R^{12}$ is preferably a naphthalene group.

As mentioned above, $R^{12}$ is preferably a phenyl group, and the polymerization unit (b) is particularly preferably a styrenic polymer. Examples of an aromatic ring-containing unit other than the styrenic polymer include the following. The styrenic polymer is a polymer obtained by polymerizing a monomeric compound comprising a styrene compound. Examples of the styrene compound include styrene, o-methylstyrene, p-methylstyrene, ethylstyrene, p-methoxystyrene, p-phenylstyrene, 2,4-dimethylstyrene, p-n-octylstyrene, p-n-decylstyrene, p-n-dodecylstyrene, chlorostyrene, bromostyrene, trimethylsilylstyrene, hydroxystyrene, 3,4,5-methoxystyrene, and pentamethyldisilylstyrene. Among others, the styrene compound is preferably at least one selected from styrene and trimethylsilylstyrene, and more preferably styrene. That is to say, the styrenic polymer is preferably at least one selected from polystyrene and poly-trimethylsilylstyrene, and is more preferably polystyrene.

In the formula (105), q is preferably 2 or more, more preferably 3 or more, and further preferably 4 or more. On the other hand, q is preferably 3000 or less, more preferably 2000 or less, and further preferably 1500 or less. The value of q in the formula (105) is preferably calculated from the value measured by gel permeation chromatography. Other measurement methods include size exclusion chromatography, a light scattering method, a viscosity method, an end-group analysis method, and a sedimentation velocity method. The molecular weight is obtained from such a measurement value, and the obtained molecular weight is then divided by the molecular weight of a unit structure to obtain the q value. At this time, the molecular weight of a unit structure can be obtained from the spectra of $^1$H-NMR. Moreover, it is more preferable to obtain a unit structure, using information regarding MS spectrum, IR spectrum and the like, as well as the information of NMR.

The polymerization unit (a) comprises at least one selected from the structure represented by the above formula (103) and the structure represented by the above formula (104). Preferably, the polymerization unit (a) mainly comprises the structure represented by the above formula (103). This is considered because the structure represented by the above formula (103) is more compact than the structure represented by the above formula (104) and thus, it becomes easy to control phase separation by the structure represented by the above formula (103).

The weight average molecular weight (Mw) of the block copolymer is preferably 500 or more, more preferably 1000 or more, and further preferably 1500 or more. On the other hand, the weight average molecular weight (Mw) of the block copolymer is preferably 1,000,000 or less, more preferably 500,000 or less, further preferably 300,000 or less, and still further preferably 250,000 or less. By setting the weight average molecular weight (Mw) of the block copolymer within the above-described range, a favorable phase-separated structure can be formed even in a case where a large-size pattern is to be formed. In addition, even in a case where a fine pattern structure is to be formed, such a pattern can be formed by a simple process. It is to be noted that the weight average molecular weight (Mw) of the block copolymer is a value measured relative to polystyrene according to GPC.

The ratio (Mw/Mn) between the weight average molecular weight (Mw) and the number average molecular weight (Mn) of the block copolymer is preferably 1 or more. On the other hand, the ratio Mw/Mn is preferably 2 or less, more preferably 1.5 or less, and further preferably 1.3 or less. By setting the ratio Mw/Mn within the above-described range, the self-assembly composition for pattern formation can form a fine, good pattern structure with higher accuracy.

The solubility of the block copolymer in at least one selected from propylene glycol monomethyl ether acetate (PGMEA) and dimethylformamide (DMF) is preferably 0.8% by mass or more, more preferably 0.9% by mass or more, and further preferably 1.0% by mass or more. The upper limit value of the solubility of the block copolymer in the above-described solvents is not particularly limited, and it can be set, for example, at 20% by mass. It is to be noted that the above-described solubility is solubility in, at least, any one selected from PGMEA, PGME, THF, butyl acetate, anisole, cyclohexanone, ethyl lactate and DMF, and the block copolymer used in the present invention preferably has solubility in any one of the above-described solvents that is a predetermined value or more.

With regard to the method of measuring the solubility of the block copolymer, while PGMEA, PGME, THF, butyl acetate, anisole, cyclohexanone, ethyl lactate, or DMF is gradually added to a predetermined amount of block copolymer, it is stirred, so that the block copolymer is dissolved in the solvent. The amount of the solvent at the time of dissolving the block copolymer therein is recorded. For stirring, a magnetic stirrer or the like may be used. The solubility is calculated according to the following equation:

Solubility (%)=mass of block copolymer/amount of solvent at time of dissolution×100

Besides, the liquid temperature of the solvent is set at 25° C., and after the solvent has been passed through a 0.2 μm PTFE hydrophobic filter, the solubility is calculated from the weight of the solution and the weight of a solid content after the removal of the solvent with an evaporator.

The solubility of the block copolymer in, at least, any one selected from PGMEA, PGME, THF, butyl acetate, anisole, cyclohexanone, ethyl lactate and DMF, which is within the above-described range, means that the polymerization degree of a sugar-derived unit constituting the sugar moiety in the formula (103) and/or the formula (104) is a predetermined value or less. Specifically, the value of r in the formula (103) and/or the formula (104) is preferably in a predetermined range or less. Thus, by controlling the polymerization degree of the sugar moiety in the formula (103) and/or the formula (104), the solubility of the block copolymer in a solvent can be enhanced, and a self-assembly composition for pattern formation having excellent phase separation ability can be obtained. Moreover, by controlling the polymerization degree of the sugar-derived unit in the formula (103) and/or the formula (104), the content rate of the sugar moiety can be easily enhanced, and thereby, the cohesive power of the polymerization unit (a) in the block copolymer can be effectively enhanced. In the case of using a block copolymer having high cohesive power, the applicable range of a pattern size of a self-assembly composition for pattern formation is widened, and also, a favorable phase-separated structure can be easily formed. Furthermore, by controlling the polymerization degree of the sugar-derived unit, it becomes possible to easily synthesize the polymerization unit (a), and consequently, the production efficiency of the block copolymer can also be enhanced.

In order to set the value of r within a predetermined range, a method of controlling the r value by regulating the length of a sugar chain before formation of a block copolymer is preferably adopted. Specifically, the length of a sugar chain is controlled by separation and purification using a silica gel column or an ion exchange resin, separation and purification involving a reverse osmosis membrane, ultrafiltration, etc., a method of cleaving a sugar chain using enzyme, or anti-solvent crystallization from oligosaccharides, so that the r value can be set within a predetermined range. Besides, the length of such a sugar chain can be confirmed, for example, using Shodex Column KS-801. Other than this method, the length of a sugar chain can also be confirmed by MULDI TOF MS, gel permeation chromatography, size exclusion chromatography, a light scattering method, a viscosity method, an end-group analysis method, a sedimentation velocity method, etc.

The content rate of the sugar moiety in the block copolymer is 3% by mass or more and 80% by mass or less based on the total mass of the block copolymer. The content rate of the sugar moiety may be 3% by mass or more, preferably 10% by mass or more, more preferably 15% by mass or more, and further preferably 25% by mass or more. On the other hand, the content rate of the sugar moiety may be 80% by mass or less, preferably 70% by mass or less, and more preferably 60% by mass or less.

Herein, the sugar moiety has a unit represented by the following formula (1) or the following formula (2). The sugar moiety consists of a single sugar-derived unit represented by the following formula (1) or the following formula (2), or is formed by polymerizing two or more sugar-derived units.

[Formula 29]

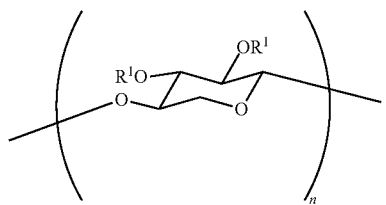

Formula (1)

[Formula 30]

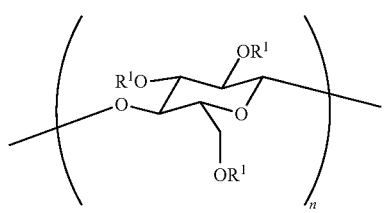

Formula (2)

In the formulae (1) and (2), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another.

The content rate of the sugar moiety in the block copolymer can be calculated by calculating the total mass of the aforementioned sugar-derived unit(s) comprised in the block copolymer, and then dividing the calculated total mass by the total mass of the block copolymer. Specifically, the content rate of the sugar moiety in the block copolymer block copolymer can be calculated according to the following equation:

Content rate of sugar moiety (% by mass)=total mass of sugar-derived unit(s)/weight average molecular weight of block copolymer×100

The total mass of the sugar-derived unit(s) can be obtained, for example, from $^1$H-NMR and the weight average molecular weight of the block copolymer. Specifically, the total mass can be calculated according to the following equation:

Total mass of sugar-derived unit(s)=polymerization degree of sugar-derived unit(s)×molecular weight of sugar That is, the content rate of the sugar moiety can be calculated according to the following equation:

Content rate of sugar moiety (% by mass)=polymerization degree of sugar-derived unit(s)×molecular weight of sugar×number of units with polymerization unit (a)/weight average molecular weight of block copolymer Herein, the number of units with the polymerization unit (a) can be calculated from the weight average molecular weight of the block copolymer, the unit ratio, and the molecular weight of each structural unit.

The block copolymer may comprise a constitutional unit having a mesogenic structure. Examples of the mesogenic structure include the following structures. In the structures, the symbol * represents a linking site.

[Formula 31]

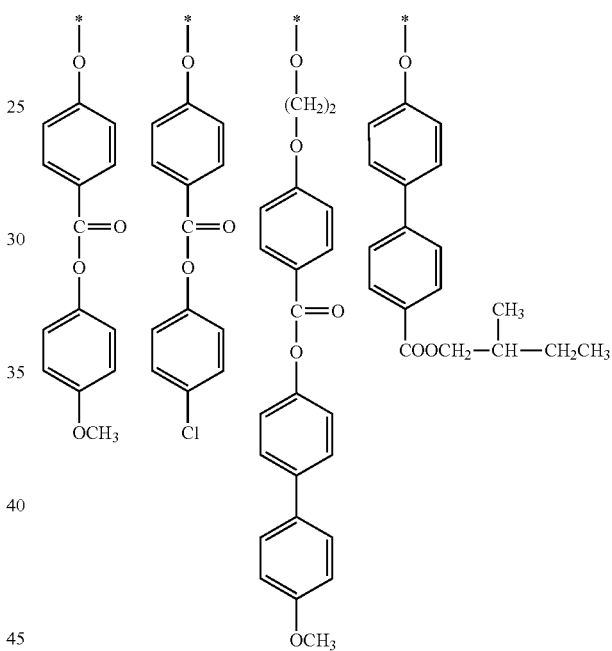

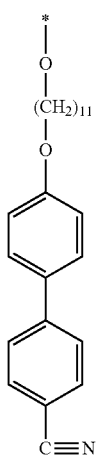

[Formula 32]

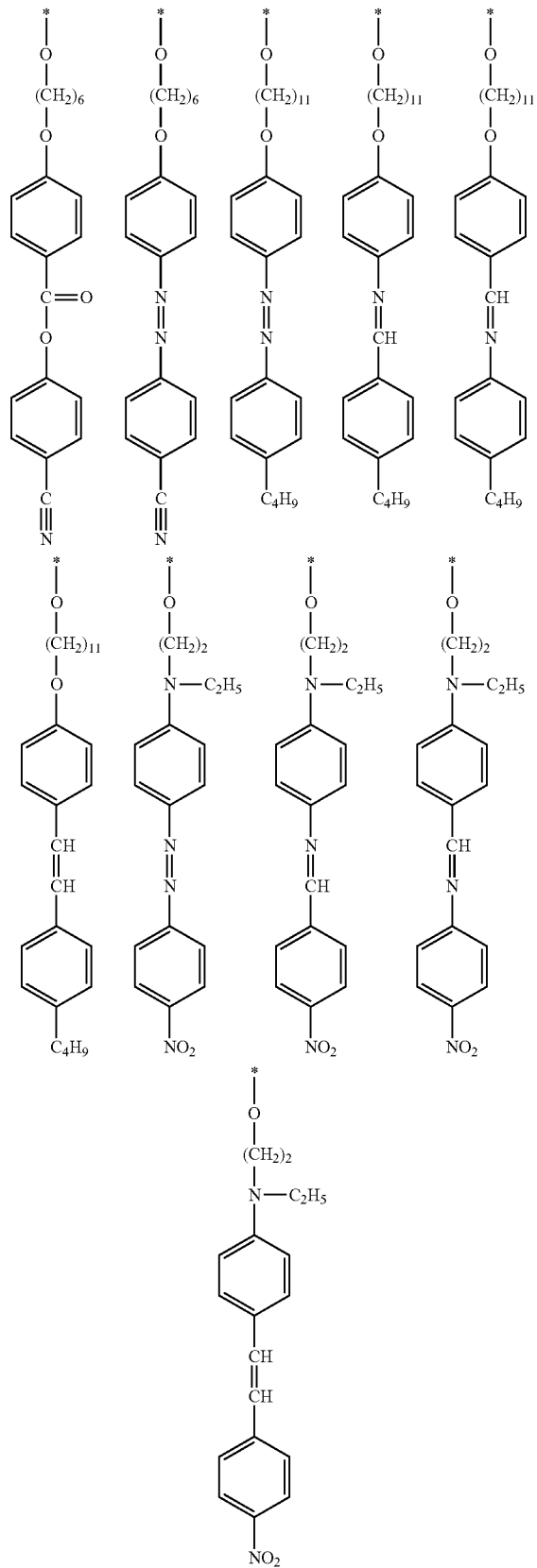

The block copolymer may also be represented by the following formula (113) or the following formula (114).

[Formula 33]

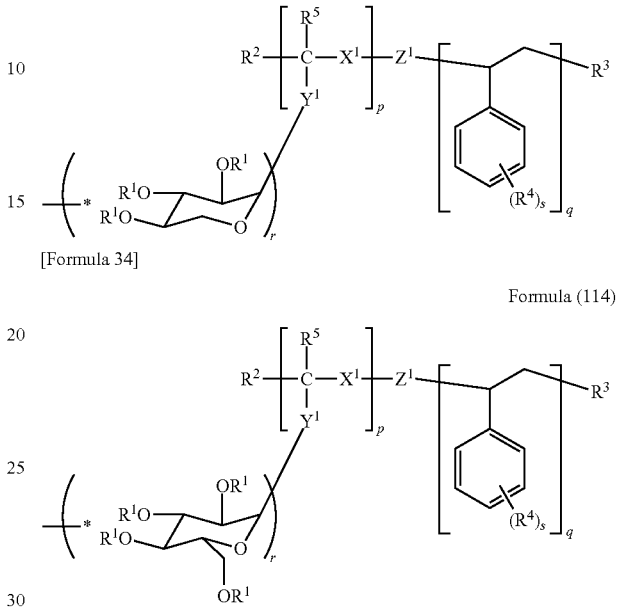

[Formula 34]

Formula (114)

In the formulae (113) and (114), $R^1$ each independently represent a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another. $R^2$ represents a hydrogen atom or a substituent; $R^3$ represents a hydrogen atom or a substituent; $R^4$ represents a halogen atom, a hydroxyl group, an alkyl group, an acyl group, a trimethylsilyl group, or a 1,1,2,2,2-pentamethyldisilyl group, wherein when s is 2 or more, a plurality of $R^4$ may be identical to or different from one another. $R^5$ represents a hydrogen atom or an alkyl group, and a plurality of $R^5$ may be identical to or different from one another. $X^1$, $Y^1$ and $Z^1$ each independently represent a single bond or a linking group, a plurality of $X^1$ may be identical to or different from one another, and a plurality of $Y^1$ may be identical to or different from one another. p represents an integer of 2 or more and 3000 or less, q represents an integer of 2 or more and 3000 or less, r represents an integer of 0 or more, at least one of a plurality of r represents an integer of 1 or more, and s represents an integer of 0 or more and 5 or less. The symbol * represents a binding site with any one of $R^1$, when r represents 2 or more, or represents a binding site with any one oxygen atom to which $R^1$ binds, instead of $R^1$.

The preferred range of $R^1$ in the formulae (113) and (114) is the same as the preferred range of $R^1$ in the formulae (103) and (104).

In the formulae (113) and (114), $R^2$ represents a hydrogen atom or a substituent. Examples of the substituent include: acyl groups such as a fluorine atom, a chlorine atom, a bromine atom, an iodine atom, a hydroxyl group, an amino group, an acetyl group, a propanoyl group, a butyryl group, an isobutyryl group, a valeryl group, an isovaleryl group, a pivaloyl group, a hexanoyl group, an octanoyl group, a chloroacetyl group, a trifluoroacetyl group, a cyclopentanecarbonyl group, a cyclohexanecarbonyl group, a benzoyl group, a methoxybenzoyl group, or a chlorobenzoyl group; and alkyl groups such as a methyl group, an ethyl group, a propyl group, an n-butyl group, a sec-butyl group, or a tert-butyl group. $R^2$ is preferably a hydrogen atom, a hydroxyl group, an acetyl group, a propanoyl group, a butytyl group, an isobutyryl group, an n-butyl group, a sec-butyl group, or a tert-butyl group, and is particularly preferably a hydrogen atom, a hydroxyl group, or a butyl group.

In addition, $R^2$ may also be, for example, a substituent having the structure represented by the aforementioned formula (105), or may further comprise the aforementioned substituent and a substituent(s) having the structure(s) represented by the aforementioned formula (103) and/or formula (104). That is to say, the block copolymer may be a polymer comprising two or more polymerization units b, or may also be a polymer having a structure of B-A-B type or B-A-B-A type.

In the formulae (113) and (114), $R^3$ represents a hydrogen atom or a substituent. Examples of the substituent include a hydrogen atom, a fluorine atom, a chlorine atom, a bromine atom, an iodine atom, a hydroxyl group, an acetyl group, a propanoyl group, a butyryl group, a methyl group, an ethyl group, a propyl group, a butyl group, an isobutyryl group, a t-butyl group, a trimethylsilyl group, and groups represented by the following structural formulae.

[Formula 35]

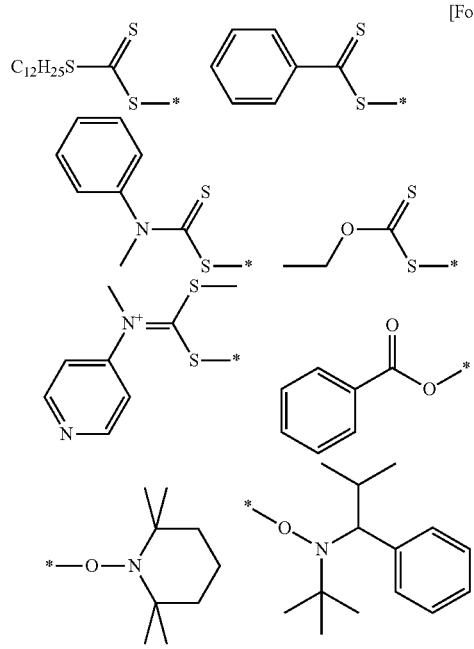

In the above structural formulae, the symbol * represents a binding site with an aromatic ring-containing unit.

In addition, $R^3$ may also be a substituent(s) having the structure(s) represented by the aforementioned formula (103) and/or formula (104), or may further comprise a substituent having the structure represented by the aforementioned formula (105). That is to say, the block copolymer may be a polymer comprising two or more polymerization units (a), or may also be a polymer having a structure of A-B-A type or A-B-A-B type.

In the formulae (113) and (114), $R^4$ represents a halogen atom, a hydroxyl group, an alkyl group, an acyl group, a trimethylsilyl group, or a 1,1,2,2,2-pentamethyldisilyl group. In the formulae, s represents an integer of 0 or more and 5 or less, and s is preferably 0. When s is 2 or more, a plurality of $R^4$ may be identical to or different from one another.

The preferred range of $R^5$ in the formulae (113) and (114) is the same as the preferred range of $R^5$ in the formulae (103) and (104).

In the formulae (113) and (114), $X^1$, $Y^1$ and $Z^1$ each independently represent a single bond or a linking group, wherein a plurality of $X^1$ may be identical to or different from one another, and a plurality of $Y^1$ may be identical to or different from one another.

$X^1$ and $Y^1$ in the formulae (113) and (114) are each independently the same as the preferred range of $X^1$ and $Y^1$ in the formulae (103) and (104).

When $Z^1$ in the formulae (113) and (114) is a linking group, examples of the linking group include —O—, an alkylene group, a disulfide group, and groups represented by the following structural formulae. When $Z^1$ is an alkylene group, the carbon atoms in the alkylene group may be substituted with heteroatoms. Examples of such a heteroatom include a nitrogen atom, an oxygen atom, a sulfur atom, and a silicon atom. In addition, when $Z^1$ is a linking group, the length of the linking group is preferably shorter than the length of the polymerization unit (a) or the polymerization unit (b).

[Formula 36]

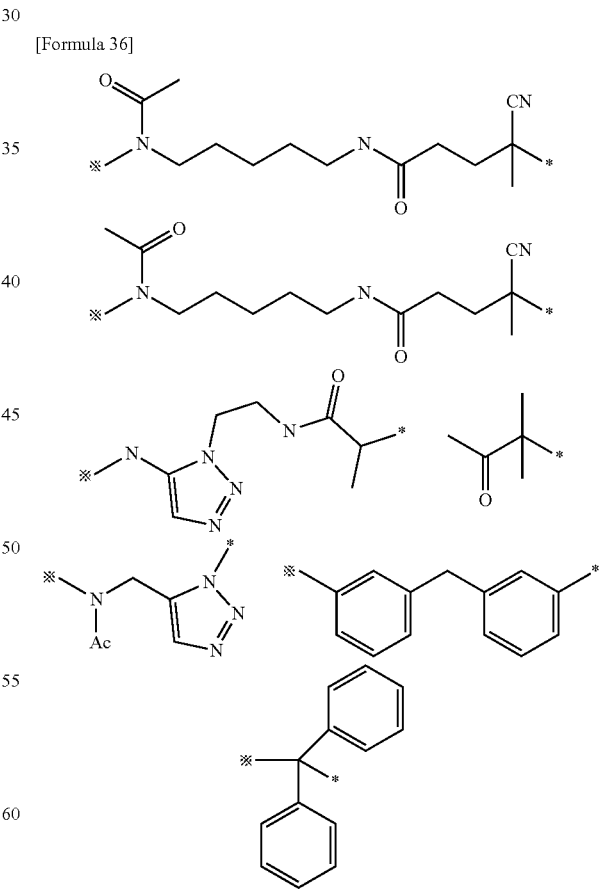

In the above structural formulae, the symbol * represents a binding site with an aromatic ring-containing unit, and the symbol ※ represents a binding site with $X^1$.

In the formulae (113) and (114), p represents an integer of 2 or more and 3000 or less, and q represents an integer of 2 or more and 3000 or less. The preferred ranges of p and q in the formulae (113) and (114) are the same as the preferred ranges of p and q in the formulae (103) to (105), respectively.

In the formulae (113) and (114), r represents an integer of 0 or more, and at least one of a plurality of r represents an integer of 1 or more. The preferred range of r in the formulae (113) and (114) is the same as the preferred range of r in the formulae (103) and (104), respectively.

The unit ratio between the polymerization unit (a) and the polymerization unit (b) in the block copolymer is preferably 1:9 to 9:1, and more preferably 1:9 to 5:5. That is, in the formulae (113) and (114), p:q is preferably 1:9 to 9:1, and more preferably 1:9 to 5:5. Besides, the above-described ratio can be adjusted, as appropriately, depending on the shape of a pattern. For instance, when the block copolymer forms a lamellar phase-separated structure, the unit ratio between the polymerization unit (a) and the polymerization unit (b) is preferably 3:7 to 7:3. On the other hand, when the block copolymer forms a cylinder-type phase-separated structure having a sugar chain therein, the component ratio between the polymerization unit (a) and the polymerization unit (b) is preferably 2:8 to 5:5. Moreover, when the block copolymer forms a cylinder-type phase-separated structure having a sugar chain outside thereof, the component ratio between the polymerization unit (a) and the polymerization unit (b) is preferably 5:5 to 9:1. It is to be noted that the unit ratio means the ratio between the number of units constituting the polymerization unit (a) and the number of units constituting the polymerization unit (b).

(Organic Solvent)

In the step of forming a self-assembly film, a self-assembly composition for pattern formation was applied to the surface of a substrate, on which an under coating agent has been applied. At this time, the self-assembly composition for pattern formation preferably comprises an organic solvent. Examples of the organic solvent include an alcohol solvent, an ether solvent, a ketone solvent, a sulfur-containing solvent, an amide solvent, an ester solvent, and a hydrocarbon solvent. These solvents may be used alone or in combination of two or more types.

Examples of the alcohol-based solvent include: methanol, ethanol, n-propanol, i-propanol, n-butanol, i-butanol, sec-butanol, tert-butanol, n-pentanol, i-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol, and diacetone alcohol; and ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, 1H,1H-trifluoroethanol, 1H,1H-pentafluoropropanol, and 6-(perfluoroethyl)hexanol.

Moreover, examples of a partially etherified polyhydric alcohol-based solvent include ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, diethylene glycol dimethyl ether, diethylene glycol ethylmethyl ether, propylene glycol monomethyl ether (PGME), propylene glycol monoethyl ether, propylene glycol monopropyl ether, propylene glycol monobutyl ether, dipropylene glycol monomethyl ether, dipropylene glycol monoethyl ether, and dipropylene glycol monopropyl ether.

Examples of the ether-based solvent include diethyl ether, dipropyl ether, dibutyl ether, diphenyl ether, and tetrahydrofuran (THF).

Examples of the ketone-based solvent include acetone, methylethyl ketone, methyl-n-propyl ketone, methyl-n-butyl ketone, diethyl ketone, methyl-i-butyl ketone, methyl-n-pentyl ketone, ethyl-n-butyl ketone, methyl-n-hexyl ketone, di-i-butyl ketone, trimethylnonanone, cyclopentanone, cyclohexanone, cycloheptanone, cyclooctanone, methylcyclohexanone, 2,4-pentanedione, acetonylacetone, acetophenone and furfural.

The sulfur-based solvent is, for example, dimethyl sulfoxide.

Examples of the amide-based solvent include N,N'-dimethylimidazolidinone, N-methylformamide, N,N-dimethylformamide, N,N-diethylformamide, acetamide, N-methylacetamide, N,N-dimethylacetamide, N-methylpropionamide, and N-methylpyrrolidone.

Examples of the ester-based solvent include diethyl carbonate, propylene carbonate, methyl acetate, ethyl acetate, γ-butyrolactone, γ-valerolactone, n-propyl acetate, i-propyl acetate, n-butyl acetate, i-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate (PGMEA), propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxytriglycol acetate, ethyl propionate, n-butyl propionate, i-amyl propionate, methyl 3-methoxypropionate, diethyl oxalate, di-n-butyl oxalate, methyl lactate, ethyl lactate, n-butyl lactate, n-amyl lactate, diethyl malonate, dimethyl phthalate, and diethyl phthalate.

Examples of the hydrocarbon-based solvent include: aliphatic hydrocarbon-based solvents such as n-pentane, i-pentane, n-hexane, i-hexane, n-heptane, i-heptane, 2,2,4-trimethylpentane, n-octane, i-octane, cyclohexane, or methylcyclohexane; and aromatic hydrocarbon-based solvents such as benzene, toluene, xylene, mesitylene, ethyl benzene, trimethyl benzene, methylethyl benzene, n-propyl benzene, i-propyl benzene, diethyl benzene, i-butyl benzene, triethyl benzene, di-i-propyl benzene, n-amyl naphthalene, or anisole.

Among these examples, propylene glycol monomethyl ether acetate (PGMEA), N,N-dimethylformamide (DMF), propylene glycol monomethyl ether (PGME), anisole, ethanol, methanol, acetone, methyl ethyl ketone, hexane, tetrahydrofuran (THF), dimethyl sulfoxide (DMSO), 1H,1H-trifluoroethanol, 1H,1H-pentafluoropropanol, 6-(perfluoroethyl)hexanol, ethyl acetate, propyl acetate, butyl acetate, cyclohexanone, and furfural are more preferable, PGMEA, PGME, THF, butyl acetate, anisole, cyclohexanone, or DMF is even more preferable, and PGMEA is further preferable. These solvents may be used alone or in combination of two or more types.

The content of such an organic solvent is preferably 10% by mass or more, more preferably 20% by mass or more, and further preferably 30% by mass or more, based on the total mass of the self-assembly composition for pattern formation. On the other hand, the content of such an organic solvent is preferably 99.9% by mass or less, and more preferably 99% by mass or less, based on the total mass of the self-assembly composition for pattern formation. By setting the content of the organic solvent within the above-described range, the coating properties of the self-assembly composition for pattern formation can be improved.

(Ionic Liquid)

Preferably, the self-assembly composition for pattern formation of the present invention further comprises an ionic liquid. The ionic liquid means a solvent, which is in the state of liquid at a temperature of 100° C. or lower and is composed of only ions. With regard to ions constituting such an ionic liquid, at least one of a cationic part and an anionic part is composed of organic ions.

By allowing the self-assembly composition for pattern formation to comprise an ionic liquid, compatibility between the block copolymer and the organic solvent can be enhanced. Moreover, the ionic liquid also has a function of promoting the phase separation of the block copolymer.

The ionic liquid consists of a cationic part and an anionic part. The cationic part of the ionic liquid is not particularly limited, and in general, those used in the cationic part of an ionic liquid can be used herein. Preferred examples of the cationic part of the ionic liquid include a nitrogen-containing aromatic ion, an ammonium ion, and a phosphonium ion.

Examples of the nitrogen-containing aromatic cation include a pyridinium ion, a pyridazinium ion, a pyrimidinium ion, a pyrazinium ion, an imidazolium ion, a pyrazonium ion, an oxazolium ion, a 1,2,3-triazolium ion, a 1,2,4-triazolium ion, a thiazolium ion, a piperidinium ion, and a pyrrolidinium ion.

Examples of the anionic portion of the ion liquid include a halogen ion, a carboxylate ion, a phosphinate ion, a phosphate ion, a phosphonate ion, and a bis(trifluoromethylsulfonyl)imide ion, and among these, a bis(trifluoromethylsulfonyl)imide ion is preferable. Examples of the halogen ion include a chloride ion, a bromide ion, and an iodide ion, and among these, a chloride ion is preferable. Examples of the carboxylate ion include a formate ion, an acetate ion, a propionate ion, a butyrate ion, a hexanoate ion, a maleate ion, a fumarate ion, an oxalate ion, a lactate ion, and a pyruvate ion, and among these, a formate ion, an acetate ion, and a propionate ion are preferable.

The content of the ionic liquid is preferably 0.1% by mass or more, more preferably 1% by mass or more, and even more preferably 2% by mass or more, based on the total mass of the self-assembly composition for pattern formation. On the other hand, the content of the ionic liquid is preferably 99% by mass or less, more preferably 98% by mass or less, and further preferably 97% by mass or less, based on the total mass of the self-assembly composition for pattern formation. By setting the content of the ionic liquid within the above-described range, compatibility between the block copolymer and the organic solvent can be enhanced. Moreover, by setting the content of the ionic liquid within the above-described range, the phase separation of the block copolymer can be promoted.

(Optional Components)

The self-assembly composition for pattern formation may further comprise optional components. The optional component is, for example, a surfactant. By allowing the self-assembly composition for pattern formation to comprise a surfactant, the coating properties of the self-assembly composition can be improved. Examples of a preferred surfactant include a nonionic surfactant, a fluorine-based surfactant, and a silicon-based surfactant. These surfactants may be used alone or in combination of two or more types.

The self-assembly composition for pattern formation may comprise monomeric components of the block copolymer. For example, in order to improve desired phase separation properties, a monomer constituting the polymerization unit (a) or a monomer constituting the polymerization unit (b) can be added, as appropriate, to the present self-assembly composition for pattern formation.

(Method for Producing Self-Assembly Composition for Pattern Formation)

<Method of Extracting Polymerization Unit (a)>

The polymerization unit (a) may be synthesized, but the synthesis may also be combined with a step of extracting it from lignocellulose or the like derived from woody plants or herbaceous plants. When the sugar moiety of the polymerization unit (a) is extracted from lignocellulose or the like derived from woody plants or herbaceous plants, the extraction method described in JP-A-2012-100546, etc. can be applied.

<Extraction of Xylooligosaccharide>

As a woody plant-derived lignocellulose raw material, the xylem or bark of broadleaf trees or coniferous trees is preferably used, but other sites such as a branch or a leaf can also be used. As a herbaceous plant-derived lignocellulose raw material, the sites of kenaf, hemp, bagasse, rice, etc., such as a stem or a leaf, can be used without any particular limitation. Upon extraction of the polymerization unit (a), it is preferable to use a fibrillated product obtained by performing a fibrillation treatment on the sites of woody plants, such as a xylem or a bark, or the sites of herbaceous plants, such as a stem, a branch or a leaf. After completion of the fibrillation treatment, the obtained product is preferably used in the form of pulp. The pulp used herein is not particularly limited, and examples thereof include chemical pulp, mechanical pulp, and deinked pulp. A broadleaf tree-derived chemical pulp is preferable. Examples of a digestion method for obtaining chemical pulp include known digestion methods such as craft digestion, polysulfide digestion, soda digestion, or alkali sulfite digestion. Taking into consideration the quality of pulp, the energy efficiency for obtaining pulp, etc., it is preferable to use the craft digestion method. In addition, it is more preferable to use pulp that is bleached with oxygen after completion of the craft digestion.

When the polymerization unit (a) is extracted from lignocellulose or the like derived from woody plants or herbaceous plants, pulp slurry is preferably subjected to an enzyme treatment, a reverse osmosis membrane treatment, an ultrafiltration treatment, or an acid treatment, and is more preferably, further subjected to an activated carbon treatment and an ion exchange treatment.

In the enzyme treatment step, a hemicellulase treatment is preferably carried out. The hemicellulase used in the present invention is not particularly limited, as long as it comprises xylanase activity. Examples of the hemicellulase include: commercially available enzyme preparations, such as, as product names, Cartazyme (manufactured by Clariant), Pulpzyme (manufactured by Novo Nordisk), Ecopulp (manufactured by Rohm Enzyme, Inc.), Sumizyme (manufactured by Shin-Nippon Chemical Industrial Co., Ltd.), Multifect Xylanase (manufactured by Genoncor Inc.), or Xylanase Conch (manufactured by Advanced Bio-Chemicals Co., Ltd.); and xylanase produced by microorganisms such as genus *Trichoderma*, genus *Thermomyces*, genus *Aureobasidium*, genus *Streptomyces*, genus *Aspergillus*, genus *Clostridium*, genus *Bacillus*, genus *Thermotoga*, genus *Thermoascus*, genus *Caldocellum*, or genus *Thermomonospora*.

In the hemicellulase treatment step, by adjusting the amount of hemicellulase added to pulp and the reaction time, the concentration of oligosaccharide eluted from the pulp and the polymerization degree of oligosaccharide can be controlled. In general, as the added amount of hemicellulase increases, or as the reaction time prolongs, the concentration of oligosaccharide in the reaction solution increases and the polymerization degree of oligosaccharide decreases. Accordingly, in order to stably obtain a high concentration of molasses containing a high polymerization degree of oligosaccharide, it is preferable that a suitable amount of hemicellulase (i.e., hemicellulase in which low-molecular-weight hemicellulase is not decomposed) be added to pulp, and that an aliquot of the molasses after completion of the reaction be returned to an enzyme reaction tank and be subjected to an enzyme reaction again. Thereby, while maintaining a high polymerization degree of oligosaccharide, the sugar concentration in the high polymerization degree of oligosaccharide can be enhanced as the time lapses.

Besides, the suitable amount of hemicellulase added to pulp and the reaction time are different depending on the type of the used enzyme. For example, in the case of multifect xylanase, the reaction time is preferable 10 minutes or longer and 240 minutes or shorter. In addition, the amount of hemicellulase added to pulp is preferably 2 units/g or more and 200 units/g or less, based on the absolute dry mass of the pulp.

The polymerization degree of oligosaccharide, which is eluted in the reaction solution obtained by subjecting pulp to a hemicellulase treatment, is fluctuated depending on the type of the used enzyme or reaction conditions. For example, in the case of using multifect xylanase, under conditions of a pulp concentration of 10% by mass, a reaction time of 45 minutes, a reaction temperature of 50° C., pH 6.0, and the amount of enzyme added to pulp that is 50 units/g, xylooligosaccharide having a polymerization degree of 1 or more and 15 or less and an average polymerization degree of approximately 5, and acidic xylooligosaccharide having a polymerization degree of 1 or more and 20 or less and an average polymerization degree of approximately 10 are eluted in molasses.

With regard to the reverse osmosis membrane treatment step, a sugar solution contained in the filtrate obtained after the reaction of pulp with hemicellulase is concentrated. In a method using a reverse osmosis membrane, low molecules such as xylose or xylobiose (sugar having a small polymerization degree) or low-molecular-weight substances contained in the molasses obtained after completion of the reaction (e.g., inorganic matters such as sodium carbonate or sodium thiosulfate, organic acids, etc.) are removed as permeates, and only high-molecular-weight substances (xylooligosaccharide having a high polymerization degree) are selectively concentrated.

An ultrafiltration membrane treatment is preferably performed on molasses that has been concentrated using a reverse osmosis membrane. In the treatment using an ultrafiltration membrane, high-molecular-weight impurities, such as raw material-derived lignin originally contained in the sugar concentrate or coloring substances, can be removed. The cutoff molecular weight of the ultrafiltration membrane is preferably 5000 or more and 30000 or less.

The molasses concentrated using a reverse osmosis membrane comprises xylooligosaccharide and acidic xylooligosaccharide. Some portions of the xylooligosaccharide and the acidic xylooligosaccharide bind to lignin and are present in the form of complexes (i.e., a lignin-xylooligosaccharide complex and a lignin-acidic xylooligosaccharide complex). Thus, an acid treatment is performed on the molasses that has been concentrated using a reverse osmosis membrane, so that xylooligosaccharide and acidic xylooligosaccharide can be released from the complexes. The acid treatment method is, for example, a method comprising adding acid to molasses to adjust pH to 5 or less, and then heating the molasses at a high temperature. The acid used in the adjustment of pH is not particularly limited, and examples of the acid include mineral acids such as sulfuric acid and hydrochloric acid, and organic acids such as oxalic acid and acetic acid. The pH applied during the acid treatment is preferably 2 or more and 5 or less. The temperature applied during the acid treatment is not particularly limited, and it is preferably 100° C. or higher and 200° C. or lower. In addition, the pressure applied during the acid treatment is preferably in the range of the atmospheric pressure or more and 5 kg/cm$^2$ or less.

In order to further reduce the content of impurities contained in the molasses after completion of the acid treatment, such as coloring substances, an activated carbon treatment is preferably carried out. The type of the activated carbon used is not particularly limited, as long as it has an ability to reduce the content of impurities contained in the molasses, such as coloring substances.

In the ion exchange treatment step, xylooligosaccharide and acidic xylooligosaccharide contained in molasses, from which impurities such as coloring substances have been reduced, are separated and/or purified using an ion exchange resin. The separation and/or purification method that can be applied herein is, for example, a method of passing a sugar concentrate containing oligosaccharide through (1) a strong cation resin, (2) a weak anion resin, (3) a strong cation resin, and (4) a weak anion resin in this order. Since acidic xylooligosaccharide is adsorbed on the anionic resin in this method, only xylooligosaccharide can be recovered as a filtrate. Subsequently, a salt solution such as sodium chloride is passed through the anion resin, so that acidic xylooligosaccharide can be eluted from the resin and can be recovered. The recovered solution containing xylooligosaccharide and acidic xylooligosaccharide can be concentrated, for example, using a concentration apparatus such as Evaporation. The solution containing oligosaccharide is dried by spray drying to obtain the powders of xylooligosaccharide and acidic xylooligosaccharide.

Xylan can be extracted by applying, for example, the method disclosed in JP-A-2012-180424.

Cellulose can be extracted by applying, for example, the method disclosed in JP-A-2014-148629.

<Formation of Derivative of Polymerization Unit (a)>

As a polymerization unit (a), the sugar moiety obtained by the above-described extraction method may be directly used, but the OH group of the sugar moiety may be modified by acetylation or halogenation and may be then used. For example, when an acetyl group is introduced into the sugar moiety, the sugar moiety is allowed to react with acetic anhydride, so that an acetylated sugar moiety can be obtained.

<Method of Synthesizing Polymerization Unit (b)>

The polymerization unit (b) may be formed by synthesis, or a commercially available product may be used as such a polymerization unit (b). In the case of polymerizing the polymerization unit (b), a known synthetic method can be adopted. On the other hand, in the case of using a commercially available product, Amino-terminated PS (Mw=12300 Da, Mw/Mn=1.02, manufactured by Polymer Source, Inc.), etc. can be used, for example.

<Coupling Reaction>

The block copolymer can be synthesized with reference to Macromolecules Vol. 36, No. 6, 2003. Specifically, a compound comprising the polymerization unit (a) and a compound comprising the polymerization unit (b) are added to a solvent such as DMF, water or acetonitrile, and a reducing agent is then added thereto. The reducing agent can be NaCNBH$_3$ or the like. Thereafter, the mixture is stirred at a temperature of 30° C. or higher and 100° C. or lower for 1 or more and 20 or less days, and a reducing agent is appropriately added to the reaction mixture, as necessary. Water is added to the reaction mixture to obtain a precipitate, and a solid content thereof is then vacuum-dried, so that a block copolymer can be obtained.

Examples of the method of synthesizing a block copolymer include synthetic methods using radical polymerization, RAFT polymerization, ATRP polymerization, click reaction, NMP polymerization, or living anion polymerization, as well as the above-described method.

The RAFT polymerization is a radical initiation polymerization reaction involving an exchange chain reaction of utilizing a thiocarbonylthio group. For example, there can be adopted a method comprising converting the OH group attached to position 1 at the terminus of xylooligosaccharide to a thiocarbonylthio group, and then allowing a styrene monomer to react with the resultant at a temperature of 30° C. or higher and 100° C. or lower to synthesize a block copolymer (Material Matters, Vol. 5, No. 1, *Saishin Kobunshi Gosei* (Latest Polymer Synthesis), Sigma-Aldrich Japan).

In the ATRP polymerization, the OH group at the terminus of sugar is halogenated, and thereafter, a metal complex [(CuCl, CuCl$_2$, CuBr, CuBr$_2$, CuI, etc.)+TPMA (tris(2-pyridylmethyl)amine)], MeTREN (tris[2-(dimethylamino)ethyl]amine), etc.), a monomer (e.g., a styrene monomer), and a polymerization initiator (2,2,5-trimethyl-3-(1-phenylethoxy)-4-phenyl-3-azahexane) are allowed to react with the sugar, so that a sugar block copolymer (e.g., a sugar-styrene block copolymer) can be synthesized.

The living anion polymerization is a method of carrying out a polymerization reaction by allowing a polymerization initiator such as n-BuLi to react with a monomer. For example, xylooligosaccharide, position β-1 at the terminus of which is halogenated, is allowed to react with a polymerization initiator, and thereafter, the resultant is then allowed to react with a styrene monomer, so that a xylooligosaccharide-styrene block copolymer can be synthesized.

The click reaction is a 1,3-dipolar azide/alkyne cycloaddition reaction of using sugar having a propargyl group and a Cu catalyst. The polymerization unit (a) and the polymerization unit (b) have a linking group comprising the following structure between them.

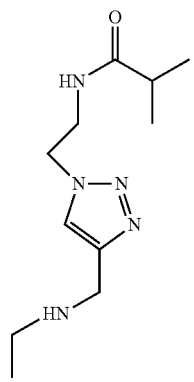

[Formula 37]

(Pattern Forming Method)

The present invention includes: a step of applying an under coating agent onto a substrate; and a step of applying a self-assembly composition for pattern formation to the surface of the substrate, onto which the under coating agent has been applied, and then forming a self-assembly film according to self-assembly phase separation. The self-assembly composition for pattern formation applied in the step of forming a self-assembly film is the aforementioned self-assembly composition for pattern formation.

In the present invention, a pattern is formed via the above-described steps, so that the pattern can be formed with high accuracy. Specifically, by forming a pattern via the above-described steps, orientation in the vertical direction (i.e., orientation in a direction vertical to the substrate) can be controlled with good accuracy. In addition, the error rate can be reduced, when a pattern position is controlled. This is considered because, in the present invention, surface free energy on the surface of a substrate can be controlled by applying an under coating agent onto the substrate, and thereby, the phase separation-forming ability of a self-assembly composition for pattern formation can be enhanced. In particular, by controlling surface free energy on the surface of the substrate, the self-assembly composition for pattern formation can be separated, with good accuracy, in a direction vertical to the substrate.

Preferably, the pattern forming method of the present invention further comprises an etching step after completion of the step of forming a self-assembly film. The etching step is a step of removing a partial phase of the self-assembly film. In the present description, the step of applying an under coating agent onto a substrate may be referred to as a "step (1)," the step of forming a self-assembly film may be referred to as a "step (2)," and the etching step may be referred to as a "step (3)."

Besides, the pattern forming method of the present invention may further comprise a step of forming a guide pattern on the substrate, between the step of applying an under coating agent onto the substrate and the step of forming a self-assembly film. Moreover, the step of forming a guide pattern on the substrate may also be established before the step of applying an under coating agent onto the substrate. The step of forming a guide pattern is a step of forming a pre-pattern on an under layer, which has been formed in the step of applying an under coating agent on a substrate.

FIGS. 1*a*-4*d* are schematic views showing the pattern-forming step. FIGS. 1*a*-1*d* shows a pattern forming method in a case where a guide hole 50 is formed as a guide pattern on a substrate 70 having an under layer 80. When the pattern-forming step includes a step of forming a guide pattern, as shown in FIG. 1(a), the guide hole 50 having a hole part 55 may be formed as a guide pattern on the substrate 70. The hole part 55 in the guide hole 50 is filled with a self-assembly composition for pattern formation 1 comprising a block copolymer 10. Besides, in FIGS. 1a-1d, an example, in which the under layer 80 is only formed on the surface of the substrate, is given. However, the under layer may be formed, not only on the surface of the substrate, but it may also be formed such that it covers the inner circumferential surface and upper surface of the hole part 55.

Figure 2A:
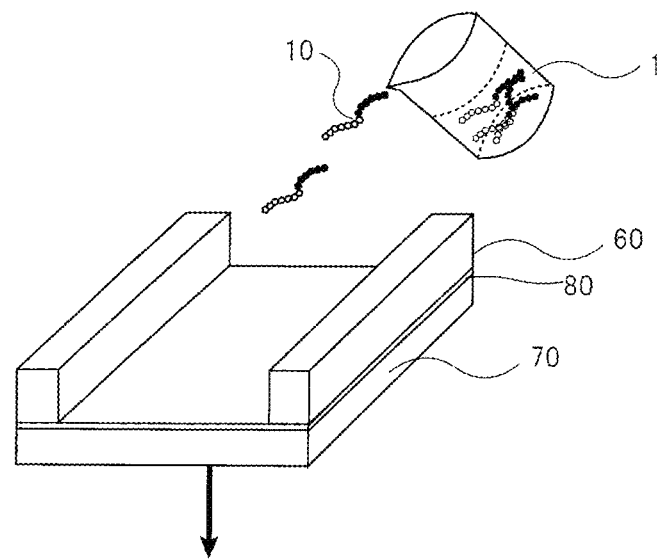
FIGS. 2A-2C are schematic views showing a pattern-forming step.

FIGS. 2a-2d show a pattern forming method in a case where linear, uneven shaped guide patterns 60 are formed on a substrate 70. In FIG. 2(a), a space (groove) between the guide patterns 60 is filled with a self-assembly composition for pattern formation 1 comprising a block copolymer 10.

FIGS. 3a-3d show a pattern forming method in a case where post guides 62 are formed as guide patterns on a substrate 70 having an under layer 80. In FIG. 3(a), a self-assembly composition for pattern formation 1 comprising a block copolymer 10 is filled into a substrate 70, such that the post guides 62 are embedded into the self-assembly composition.

FIGS. 4a-4d show a pattern forming method in a case where a guide hole 50 is formed as a guide pattern on a substrate 70 having an under layer 80. In FIGS. 4a-4d, a hole part 55 in a guide hole 50 is filled with a self-assembly composition for pattern formation 1 comprising a block copolymer 10. Besides, a difference between FIGS. 1a-1d and FIGS. 4a-4d is that one phase P and one phase Q are formed in the hole part 55 in FIGS. 1a-1d, whereas a plurality of phases Q are formed in FIGS. 4a-4d. FIGS. 4a-4d show a pattern forming method in a case where the diameter of the guide hole 50 is longer than the molecular length of the block copolymer 10. In FIGS. 4a-4d, the number of phases Q formed in the hole part 55 is preferably 2 or more and 500 or less, more preferably 2 or more and 50 or less, and further preferably 1 or more and 7 or less. By setting the number of phases Q formed in the hole part 55 within the above-described range, a pattern is easily formed to have a desired shape. Also in FIGS. 2a-4d, the under layer 80 may be formed on the surface of a guide pattern. By allowing the block copolymer 10 to come into contact with the under layer 80, phase separation performance is easily improved.

The guide pattern may have a hole shape as shown in FIGS. 1a-1d, or may also have a linear, uneven shape as shown in FIGS. 2a-2d. When the guide pattern has a hole shape, the preferred internal diameter is, for example, preferably 1 nm or more and 300 nm or less, and more preferably 5 nm or more and 200 nm or less. When the guide pattern has a linear, uneven shape, the width of a concave portion is preferably 1 nm or more and 300 nm or less, and more preferably 5 nm or more and 200 nm or less. The guide pattern needs to have a pattern shape that is equivalent to or greater than a pattern to be formed.

The hole shape of the guide hole may be a perfect circle or an ellipse. Otherwise, the hole shape may also be a plurality of perfect circles that are connected with one another. Based on the relationship between the molecular length (L0) of the block copolymer and the size (diameter) of the guide hole, a phase-separated shape varies in the guide hole. In the case of the hole shape as shown in FIG. 1, the diameter of the hole is preferably 1.5 to 2.5 times larger than the molecular length L0 of the block copolymer. Herein, the molecular length L0 of the block copolymer can be measured using a small-angle X-ray scattering method (SAXS). Moreover, in the case of the hole shape as shown in FIGS. 4a-4d, the length of the major axis of the ellipse of the guide hole is preferably 3 to 5 times longer than the molecular length L0 of the block copolymer, and the length of the minor axis of the ellipse of the guide hole is preferably 1.5 to 2.5 times longer than the molecular length L0 of the block copolymer.

The diameter of the post guide 62 as shown in FIGS. 3a-3d is preferably 5 nm or more and 300 nm or less, and more preferably 6 nm or more and 200 nm or less. Moreover, the height of the post guide 62 is preferably 5 nm or more and 300 nm or less, and more preferably 6 nm or more and 200 nm or less.

The post guide 62 can be appropriately arranged, such that a desired phase-separated pattern structure can be obtained. The post guide 62 may be arranged, such that the arrangement pattern can be a hexagonal lattice arrangement. In the case of such a hexagonal lattice arrangement, the preferred interval between the post guides 62 is preferably 1.5 to 20 times, more preferably 1.5 to 10 times, and further preferably 1.5 to 7 times larger than the molecular length L0 of the block copolymer. As the interval between the post guides 62 decreases, a phase-separated pattern having higher positional accuracy can be obtained.

Besides, as a guide pattern forming method, a physical guide (graphoepitaxy) as described in FIGS. 1a-4d may be used, or a chemical guide (chemical epitaxy) may also be used. As a method of forming a chemical guide, the method described in Japanese Patent No. 5729537 can be applied, for example.

The material of a member that forms a guide pattern is not particularly limited. For example, inorganic materials such as Si, $SiO_2$, $Al_2O_3$, AlN, GaN or glass may be used, or commercially available resist materials may also be used.

Examples of the substrate used in the pattern forming method of the present invention include substrates such as glass, silicon, SiN, GaN or AlN. Otherwise, substrates consisting of organic materials such as PET, PE, PEO, PS, a cycloolefin polymer, polylactic acid or a cellulose nanofiber may also be used. Moreover, a plurality of layers consisting of different materials may be sandwiched between the substrate and the guide pattern-forming layer. Such materials are not particularly limited, and examples of the materials include inorganic materials such as $SiO_2$, SiN, $Al_2O_3$, AlN, GaN, GaAs, W, SOC or SOG, and organic materials such as commercially available adhesives.

<Step (1)>

The pattern forming method of the present invention comprises a step of applying an under coating agent onto a substrate. The step of applying an under coating agent onto a substrate is a step of applying an under coating agent onto a substrate to form an under layer.

The under coating agent is preferably a resin composition, and examples of such a resin composition include a photosensitive resin composition, a thermally polymerized resin composition, a chemically amplified positive resist composition, a novolac resist composition, and a non-photosensitive, non-thermally polymerized resin composition.

Examples of the non-photosensitive, non-thermally polymerized resin composition include an aromatic ring-containing monomer having a vinyl group and a non-aromatic ring-containing monomer having a vinyl group. Also, an aromatic ring-containing monomer having a (meth)acryloyl group and a non-aromatic ring-containing monomer having a (meth)acryloyl group are preferably used.

The under coating agent preferably comprises a polymer containing at least one selected from a (meth)acrylate-derived unit optionally having a substituent and a styrene-derived unit optionally having a substituent. The under coating agent may comprise a polymer containing a unit that constitutes a polymer contained in the aforementioned self-assembly composition for pattern formation. Moreover, the under coating agent may also comprise a polymer containing a constitutional unit that comprises a partial structure of a unit constituting a polymer comprised in the aforementioned self-assembly composition for pattern formation or a structure similar to the structure of a unit constituting such a polymer. For example, the under coating agent may comprise a polymer containing a constitutional unit, in which the sugar moiety in the above formula (103) or formula (104) is converted to a substituent other than sugar. Examples of such a substituent include a methyl group, an ethyl group, a propyl group, an isopropyl group, a butyl group, an isobutyl group, a t-butyl group, a hydroxymethyl group, a 2-hydroxyethyl group, a methoxymethyl group, and a 2-methoxymethyl group. Such a polymer may be a homopolymer, but is preferably a random polymer.

The under coating agent more preferably comprises a polymer containing at least one selected from structures represented by the following formulae (203) to (206). Such a polymer is further preferably a random polymer.

[Formula 38]

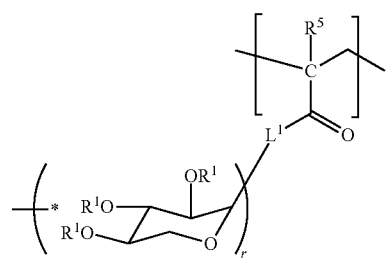

Formula (203)

[Formula 39]

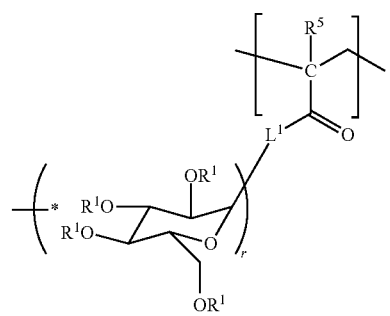

Formula (204)

[Formula 40]

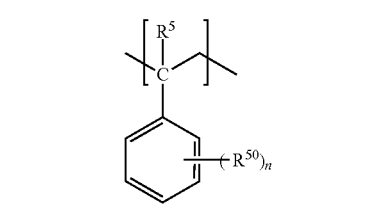

Formula (205)

[Formula 41]

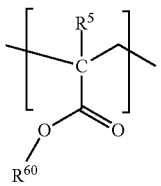

Formula (206)

In the formulae (203) and (204), $L^1$ represents —O—, —S—, —NH—, —O—$(CH_2)_n$—O—, or —O—$(CH_2)_n$—N—(C=O)—N—, provided that n represents an integer of 1 or more and 10 or less; $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another; $R^5$ represents a hydrogen atom or an alkyl group; r represents an integer of 1 or more, and the symbol * represents a binding site with any one of $R^1$, or a binding site with any one oxygen atom to which $R^1$ binds, instead of $R^1$, when r represents 2 or more.

In the formula (205), $R^5$ represents a hydrogen atom or an alkyl group, $R^{50}$ represents an organic group or a hydroxyl group, and n represents an integer of 0 to 5. In the formula (206), $R^5$ represents a hydrogen atom or an alkyl group, and $R^{60}$ represents an alkyl group.

In the formulae (203) and (204), $L^1$ represents —O—, —S—, —NH—, —O—$(CH_2)_n$—O—, or —O—$(CH_2)_n$—N—(C=O)—N—. In the above formulae, n represents an integer of 1 or more and 10 or less, and n is preferably an integer of 1 or more and 4 or less. Among others, $L^1$ is preferably —O—.

In the formulae (203) and (204), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another. Among others, preferably, $R^1$ is each independently a hydrogen atom or an acyl group containing 1 or more and 3 or less carbon atoms. The above-described alkyl group also comprises a sugar chain. That is to say, the sugar chain portion of the polymerization unit (a) may further have a branched chain.

When $R^1$ is an alkyl group or an acyl group, the number of carbon atoms possessed by the group can be selected, as appropriate, depending on purpose. For example, the number of carbon atoms is preferably 2 or more, and is also preferably 200 or less, more preferably 100 or less, further preferably 20 or less, and particularly preferably 4 or less.

Specific examples of $R^1$ include: acyl groups such as an acetyl group, a propanoyl group, a butyryl group, an isobutyryl group, a valeryl group, an isovaleryl group, a pivaloyl group, a hexanoyl group, an octanoyl group, a chloroacetyl group, a trifluoroacetyl group, a cyclopentanecarbonyl group, a cyclohexanecarbonyl group, a benzoyl group, a methoxybenzoyl group, or a chlorobenzoyl group; and alkyl groups such as a methyl group, an ethyl group, a propyl group, a butyl group, or a t-butyl group. Among these groups, an acetyl group, a propanoyl group, a butyryl group, and an isobutyryl group are preferable, and an acetyl group is particularly preferable.

In the formulae (203) and (204), $R^5$ represents a hydrogen atom or an alkyl group. Among others, $R^5$ is preferably a hydrogen atom or an alkyl group containing 1 or more and 3 or less carbon atoms, and is particularly preferably a hydrogen atom or a methyl group.

The preferred range of $R^5$ in the formulae (205) and (206) is also the same as the preferred range of $R^5$ in the formulae (203) and (204).

In the formula (205), $R^{50}$ represents an organic group or a hydroxyl group. When $R^{50}$ is an organic group, $R^{50}$ is preferably a hydrocarbon group optionally having a substituent, and more preferably an alkyl group optionally having a substituent. The hydrocarbon group optionally having a substituent may be, for example, a hydrocarbon group, in which any of carbon atoms constituting the hydrocarbon group is substituted with an oxygen atom, a silicon atom, a nitrogen atom, a sulfur atom, a halogen, etc. For example, $R^{50}$ may be a trimethylsilyl group, a pentamethyldisilyl group, a trifluoromethyl group, or a pentafluoroethyl group. When $R^{50}$ represents a hydroxyl group, the structure represented by the formula (205) is preferably a hydroxystyrene-derived constitutional unit.

In the formula (205), n represents an integer of 0 to 5, preferably an integer of 0 to 3, and particularly preferably 1.

A preferred example of the structure represented by the formula (205) may be the structure represented by the following structural formula:

[Formula 42]

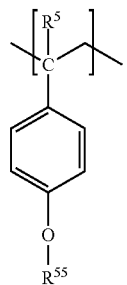

In the above structural formula, $R^5$ represents a hydrogen atom or an alkyl group, and $R^{55}$ is preferably a hydrogen atom or an alkyl group optionally having a substituent. This alkyl group comprises a sugar constitutional unit or a sugar chain.

In the formula (206), $R^{60}$ represents an alkyl group. $R^{60}$ is preferably an alkyl group containing 1 or more and 5 or less carbon atoms, more preferably an alkyl group containing 1 or more and 3 or less carbon atoms, and particularly preferably a methyl group.

In addition, $R^{60}$ may be an alkyl group having a substituent Examples of the alkyl group having a substituent include methyl, ethyl, propyl, isopropyl, butyl, isobutyl, t-butyl, —CH$_2$—OH, —CH$_2$—O-methyl, —CH$_2$—O-ethyl, —CH$_2$—O-propyl, —(C=O)—O—CH$_2$—O-isopropyl, —(C=O)—O—CH$_2$—Obutyl, —CH$_2$—O-isobutyl, —CH$_2$—O-t-butyl, —CH$_2$—O—(C=O)-methyl, —CH$_2$—O—(C=O)-ethyl, —CH$_2$—O—(C=O)-propyl, —CH$_2$—O—(C=O)-isopropyl, —CH$_2$—O—(C=O)-butyl, —CH$_2$—O—(C=O)-isobutyl, —CH$_2$—O—(C=O)-t-butyl, —C$_2$H$_4$—OH, —C$_2$H$_4$—O-methyl, —C$_2$H$_4$—O-ethyl, —C$_2$H$_4$—O-propyl, —C$_2$H$_4$—O-isopropyl, —C$_2$H$_4$—O-butyl, —C$_2$H$_4$—O-isobutyl, —C$_2$H$_4$—O-t-butyl, —C$_2$H$_4$—O—(C=O)-methyl, —C$_2$H$_4$—O—(C=O)-ethyl, —C$_2$H$_4$—O—(C=O)-propyl, —C$_2$H$_4$—O—(C=O)-isopropyl, —C$_2$H$_4$—O—(C=O)-butyl, —C$_2$H$_4$—O—(C=O)-isobutyl, and —C$_2$H$_4$—O—(C=O)-t-butyl.

The under coating agent may comprise a constitutional unit having a mesogenic structure. Examples of the mesogenic structure include the following structures. In the structures, the symbol * represents a linking portion.

[Formula 43]

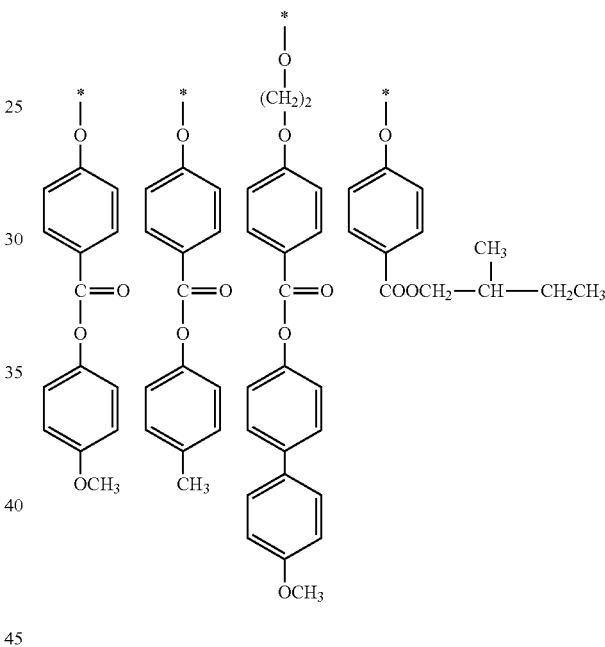

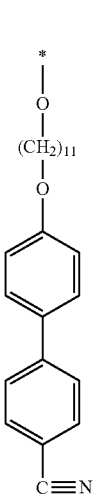

-continued

[Formula 44]

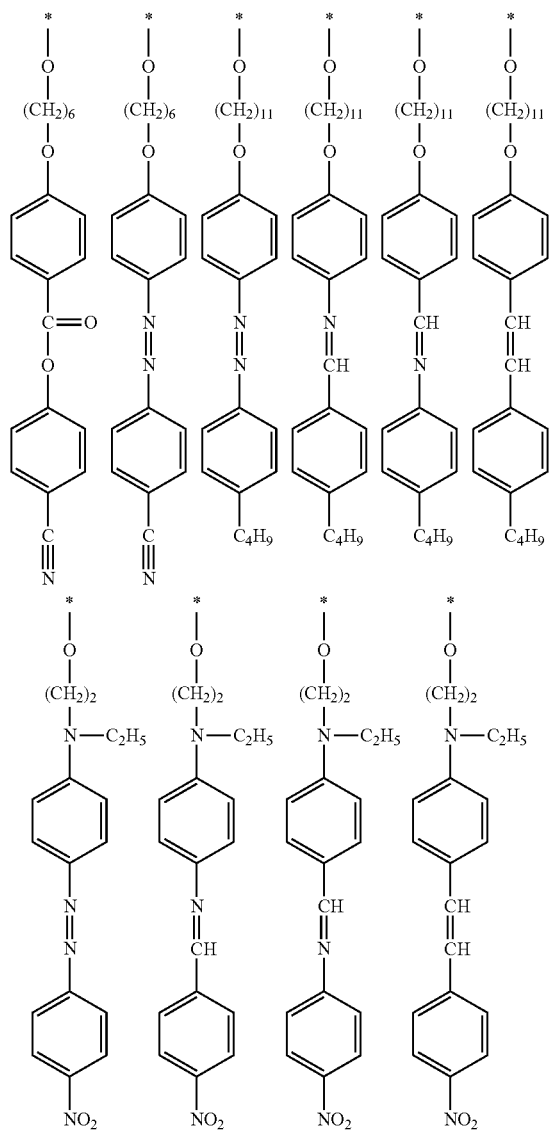

The weight average molecular weight of a polymer contained in the under coating agent is preferably 3000 or more and 300,000 or less. In addition, the ratio (Mw/Mn) between the weight average molecular weight (Mw) and the number average molecular weight (Mn) of the polymer is preferably 1 or more. On the other hand, the ratio Mw/Mn is preferably 2 or less, more preferably 1.5 or less, and further preferably 1.3 or less. By setting the ratio Mw/Mn of the polymer contained in the under coating agent within the above-described range, the self-assembly composition for pattern formation can form a fine, good pattern structure with higher accuracy. It is to be noted that the weight average molecular weight (Mw) of the polymer is a value measured relative to polystyrene according to GPC.

The polymer contained in the under coating agent can be synthesized according to a known polymerization method such as living radical polymerization, living anion polymerization, or atom transfer radical polymerization. For example, in the case of living radical polymerization, a polymerization initiator such as AIBN (α,α'-azobisisobutyronitrile) is used, and the polymerization initiator is allowed to react with a monomer to obtain a polymer. In the case of living anion polymerization, butyl lithium is allowed to react with a monomer in the presence of lithium chloride to obtain a polymer. In the present Examples, an example of synthesizing the polymer according to living anion polymerization is given. However, the synthesis method is not limited thereto, and the polymer contained in the under coating agent can be synthesized, as appropriate, according to each of the above-described synthesis methods or known synthesis methods.

Alternatively, a commercially available product may also be used as a polymer contained in the under coating agent. Examples of such a commercially available product include random polymers and homopolymers, such as P9128D-SMMAran, P9128C-SMMAran, Poly(methyl methacrylate), P9130C-SMMAran, and P7040-SMMAran, which are manufactured by Polymer Source. Inc.

The method of applying an under coating agent is not particularly limited. For example, the under coating agent may be applied onto a substrate according to a known method such as a spin-coating method. In addition, after application of the under coating agent, the under coating agent may be hardened by light exposure and/or heating, so as to form an under layer. Examples of the radiation used in the light exposure include visible light, ultraviolet light, far-ultraviolet light, X-ray, electron beam, γ-ray, molecular beam, and ion beam. In addition, the temperature applied upon heating the coated film is not particularly limited, and it is preferably 90° C. or higher and 550° C. or lower. Besides, the film thickness of the under layer is not particularly limited, and it is preferably 1 nm or more and 20000 nm or less, more preferably 1 nm or more and 1000 nm or less, further preferably 1 nm or more and 500 nm or less, and particularly preferably 1 nm or more and 50 nm or less. Further, the above-described under layer may comprise a SOC (Spin on carbon) film.

Before the under coating agent is applied onto the substrate, a step of washing the substrate is preferably established. By washing the surface of the substrate, the coating properties of the under coating agent are improved. As a washing treatment method, a conventionally known method can be applied. Examples of such a conventionally known washing method include an oxygen plasma treatment, an ozone oxidation treatment, an acid alkali treatment, and a chemical modification treatment.

After the under layer has been formed, the under layer may be rinsed, as necessary, using a rinsing solution such as a solvent. Since an uncrosslinked portion, etc. in the under layer is removed by such a rinsing treatment, the affinity with the block copolymer contained in the self-assembly composition for pattern formation is improved, and a phase-separated structure consisting of a structure oriented in the direction vertical to the surface of the substrate is easily formed.

The rinsing solution is not particularly limited, as long as it is able to dissolve an uncrosslinked portion. Thus, solvents such as propylene glycol monomethyl ether acetate (PG-MEA), propylene glycol monomethyl ether (PGME), ethyl lactate (EL) or cyclohexanone, commercially available thinner liquids, or the like can be used. Moreover, after completion of the washing, post-baking may be carried out to volatilize the rinsing solution. The temperature conditions for this post-baking are preferably 80° C. or higher and 300° C. or lower, and the baking time is preferably 30 seconds or more and 600 seconds or less.

When the pattern-forming step includes a step of forming a guide pattern, such a step of forming a guide pattern may be established before the step of applying an under coating agent, or may be established after the step of applying an under coating agent. When the step of forming a guide pattern is established before the step of applying an under coating agent, in the step of applying the under coating agent onto a substrate, the under coating agent is not only applied onto the exposed substrate, but it is also applied to the surface of a guide pattern. In the present description, when the step of forming a guide pattern is established before the step of applying an under coating agent, "the surface of the substrate, onto which the under coating agent has been applied" means "the surface of the substrate and the surface of the guide pattern, onto which the under coating agent has been applied."

In the step of forming a guide pattern, a method similar to a known resist pattern forming method can be applied. As a composition for forming a guide pattern, a conventional composition for forming a resist film can be used. As a specific method of forming a guide pattern, for example, a commercially available chemically amplified resist composition is applied onto the above-described under layer to form a resist film. Subsequently, radiation is applied to a desired region of the resist film via a mask with a specific pattern, and immersion exposure, etc. is then carried out. Examples of the above-described radiation include ultraviolet light, far-ultraviolet light, X-ray, and charged particle beam. Among these, far-ultraviolet light is preferable, ArF excimer laser light and KrF excimer laser light are more preferable, and ArF excimer laser light is further preferable. Subsequently, post-exposure baking (PEB) is carried out, and development is then carried out using a developing solution such as an alkaline developing solution, so as to form a desired guide pattern. Moreover, the guide pattern can also be formed by applying a nanoimprint technique.

Besides, a hydrophobic treatment or a hydrophilic treatment may be performed on the surface of the above-described guide pattern. The specific treatment method is, for example, a hydrogenation treatment, in which the surface of the guide pattern is exposed to hydrogen plasma for a predetermined period of time. Onto the surface of the above-described guide pattern, an under coating agent may be applied.

Since the pattern forming method comprises a step of applying an under coating agent, the phase separation of a self-assembly composition for pattern formation can be precisely controlled, and a phase-separated structure can be easily formed without forming a guide pattern. When a guide pattern is formed, a pattern can be formed with higher accuracy.

<Step (2)>

The step of forming a self-assembly film according to self-assembly phase separation (step (2)) is a step of forming a self-assembly film having a phase-separated structure, using a self-assembly composition for pattern formation. In a case where the aforementioned guide pattern is not used, the self-assembly composition for pattern formation is directly applied onto a substrate, on which an under layer has been established, thereby forming a coated film, so as to form a self-assembly film having a phase-separated structure. On the other hand, in a case where the aforementioned guide pattern is used, a self-assembly composition for pattern formation is used to form a coated film in a region on the under layer sandwiched between the guide patterns, and a self-assembly film with a phase-separated structure, which has an interface roughly vertical to the substrate, is formed on an under layer film formed on the substrate. Otherwise, in a case where a coated film of under layer is formed on a guide pattern, a self-assembly composition for pattern formation is applied onto the aforementioned coated film, so as to form a coated film.

In the step (2), annealing or the like is carried out on the self-assembly composition for pattern formation that has been applied onto the substrate, so that polymers having the same properties are accumulated with one another to spontaneously form an order pattern, thereby forming a self-assembly film having a phase-separated structure such as a sea-island structure, a cylinder structure, a co-continuous structure or a lamellar structure. Since the self-assembly composition for pattern formation of the present invention has high cohesive power and can form a favorable phase-separated structure, it becomes possible to achieve sufficient phase separation in a shorter annealing time.

The annealing method is, for example, a method of heating the self-assembly composition for pattern formation at a temperature of 80° C. or higher and 400° C. or lower, using an oven, a hot plate, a microwave, etc. The annealing time is generally 10 seconds or longer and 30 minutes or shorter. With regard to annealing conditions, as the content of the sugar moiety increases, it becomes possible to shorten the annealing time or to decrease the annealing temperature. For example, when the self-assembly composition for pattern formation is heated with a hot plate, it is preferable to carry out the annealing treatment under conditions of a temperature of 100° C. or higher and 300° C. or lower and an annealing time of 10 seconds or more and 20 minutes or less. The film thickness of the self-assembly film obtained by this treatment is preferably 0.1 nm or more and 1000 nm or less, and more preferably 0.1 nm or more and 500 nm or less.

Figure 1B:
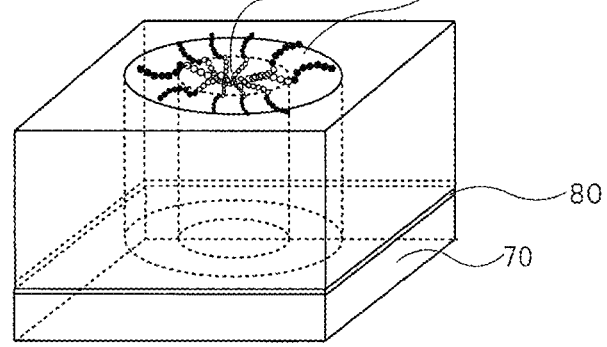
Figure 1C:
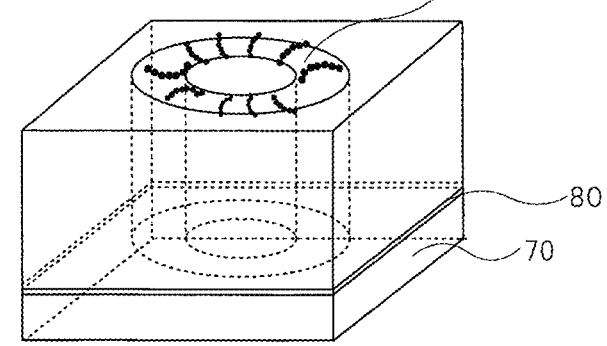
Figure 2B:
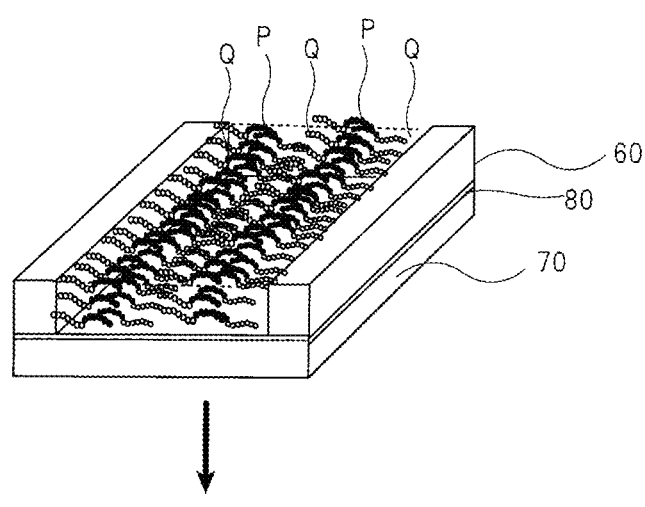
Figure 2C:
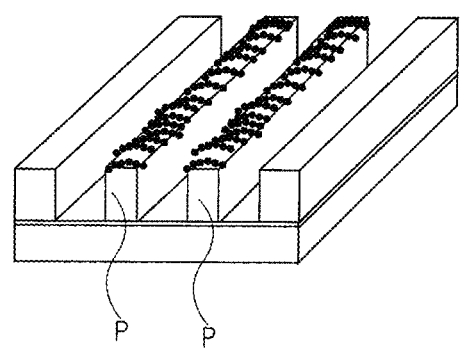
Figures 4A, 4B, 4C, 4D:
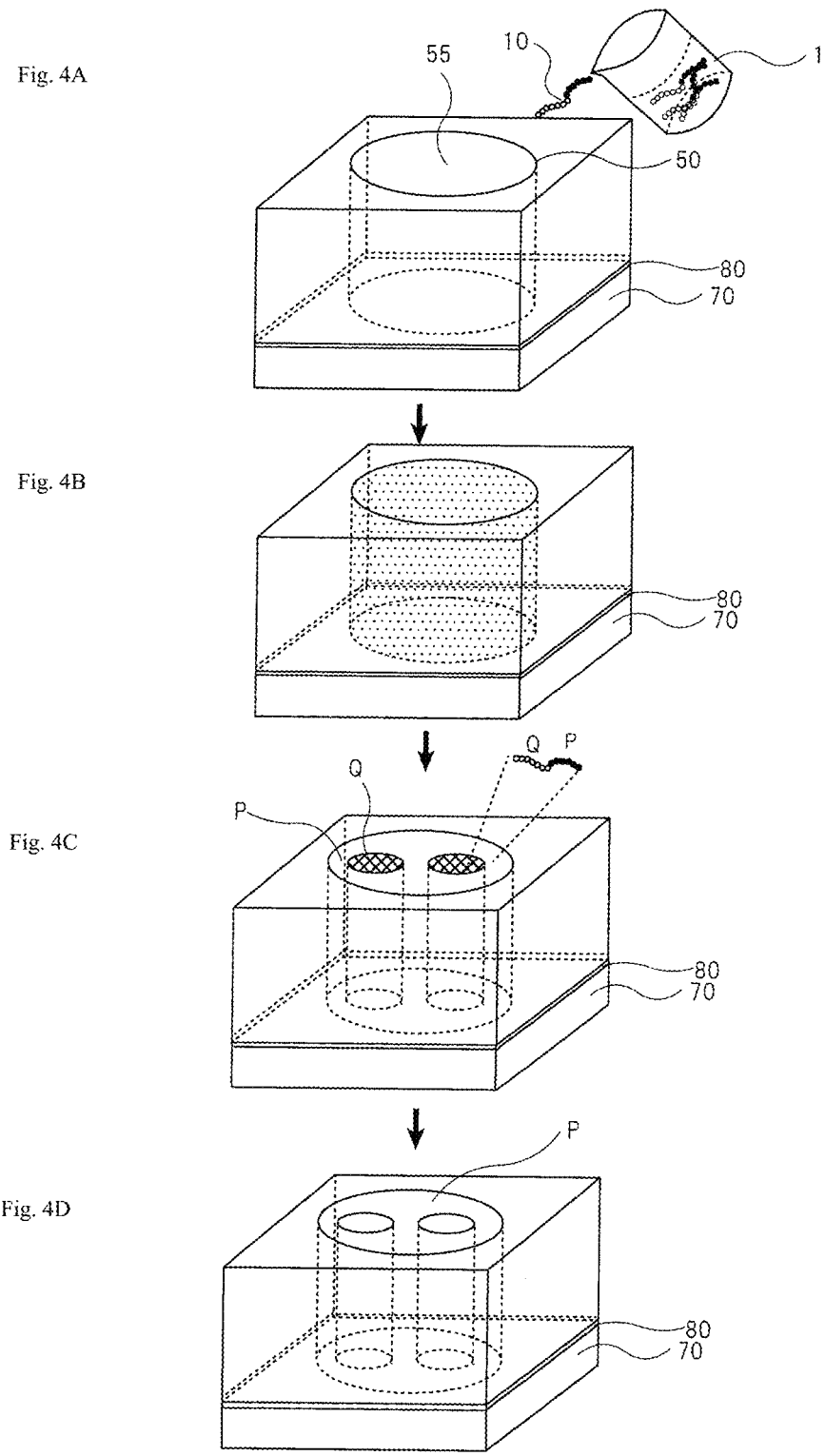
FIGS. 4A-4D are schematic views showing a pattern-forming step.

The annealing step is preferably established, in FIGS. 1a-1d, when the condition shown in FIG. 1(a) is converted to the condition shown in FIG. 1(b), or in FIGS. 2a-2d, when the condition shown in FIG. 2(a) is converted to the condition shown in FIG. 2(b), or in FIGS. 3a-3d, when the condition shown in FIG. 3(b) is converted to the condition shown in FIG. 3(c), or in FIGS. 4a-4d, when the condition shown in FIG. 4(b) is converted to the condition shown in FIG. 4(c). By phase separation of the block copolymer in the annealing step, a phase-separated structure is formed. When the pattern-forming step includes a step of forming a guide pattern, as shown in FIG. 1(b) for example, the phase is separated into the phase P on the outer peripheral side and the phase Q on the inner peripheral side. At this time, phase separation is preferably carried out, so that the block copolymer becomes a cylindrical shape. When the guide pattern has a linear, uneven shape, the separated phase P and the separated phase Q are separated from each other in layers, as shown in FIG. 2(b). At this time, phase separation is preferably carried out, so that the block copolymer becomes a lamellar shape. In FIG. 3(c), the phase is separated into the phase P on the outer peripheral side and the phase Q on the inner peripheral side, so that a hexagonal close-packed structure can be formed having the post guide 62 as a center. On the other hand, in FIG. 4(c), the phase P is separated from the phase Q, so that a plurality of the phases Q can be formed in the guide hole 50. In the present invention, the phase P is preferably composed of a polymerization unit (b) comprising at least two or more aromatic ring-containing units, and the phase Q is preferably composed of a polymerization unit (a) comprising two or more units of at least one type selected from a glucose unit and a xylose unit. Besides, when not a hole pattern, but a pillar pattern is to be formed in FIGS.

1a-1d, FIGS. 3a-3d, and FIGS. 4a-4d, the phase P is preferably composed of a polymerization unit (a) comprising two or more units of at least one type selected from a glucose unit and a xylose unit, and the phase Q is preferably composed of a polymerization unit (b) comprising at least two or more aromatic ring-containing units.

The method of applying the self-assembly composition for pattern formation onto a substrate to form a coated film is not particularly limited. An example of the method of forming such a coated film is a method of applying the used self-assembly composition for pattern formation onto a substrate according to a spin-coating method. According to this method, the self-assembly composition for pattern formation is applied onto the above-described substrate, or between guide patterns on the above-described under layer, thereby forming a coated film.

<Step (3)>

The etching step (step (3)) is a step of removing a partial phase from the self-assembly film. This removal is carried out by an etching treatment of utilizing a difference in the etching rates of individual phases that have been separated by directed self-assembling (P and Q in FIGS. 1a-4d). FIG. 1(c), FIG. 2(c), FIG. 3(d), and FIG. 4(d) show the state of a phase-separated structure, from which the phase Q has been removed.

Examples of the method of removing a partial phase from the self-assembly film by the etching step include known etching methods including: reactive ion etching (RIE) such as chemical dry etching or chemical wet etching (wet development); and physical etching such as sputter etching or ion beam etching. Among these etching methods, for example, a dry etching step using $O_2$ gas or the like is preferably adopted as a method of removing a phase consisting of a polymerization unit comprising two or more units of at least one type selected from a glucose unit and a xylose unit. In addition, a chemical wet etching step can also be adopted. Examples of such a wet etching method include a method of treating a partial phase by allowing the phase to react with acetic acid, a method of treating a partial phase by allowing the phase to react with a mixed solution of water and alcohol such as ethanol or i-propanol, and a method comprising applying UV light or EB light to a partial phase and then treating it with acetic acid or alcohol.

The etching step may comprise a step of removing a guide pattern. The method of removing a guide pattern is not particularly limited. For example, a method of removing a guide pattern by an etching treatment of utilizing a difference in the etching rates between the guide pattern and the formed self-assembly film can be applied.

Before the etching step, a process of introducing a metal into a hydrophilic portion (sugar moiety), such as an SIS process (Sequential Infiltration Synthesis), may be established. Examples of the metal to be introduced include Li, Be, Na, Mg, Al, Si, K, Ca, Sc, Ti, V, Cr, Mn, Fe, Co, Ni, Cu, Zn, Ga, Ge, As, Rb, Sr, Y, Zr, Nb, Mo, Ru, Pd, Ag, Cd, In, Sn, Sb, Te, Cs, Ba, La, Hf, Ta, W, Re, Os, Ir, Pt, Au, Hg, Tl, Pb, Bi, Po, Ce, Pr, Nd, Pm, Sm, Eu, Gd, Tb, Dy, Ho, Er, Tm, Yb, and Lu. Such a process can be carried out according to the method described, for example, in Journal of Photopolymer Science and Technology Volume 29, Number 5 (2016) 653-657. In such a case, not a hydrophilic portion but a hydrophobic portion is removed by the etching step.

The pattern can be formed as described above. The formed pattern is preferably a line-and-space pattern, a hole pattern, or a pillar pattern. According to the pattern forming method of the present invention, since the aforementioned self-assembly composition for pattern formation is used, a favorable phase-separated structure can be formed even in the case of forming a large size pattern. In addition, the thus formed pattern is used as a mask, so that a pattern shape can be formed on a Si substrate.

(Under Coating Agent)

The present invention may also relate to an under coating agent, which is used for the phase separation of a self-assembly composition for pattern formation. The under coating agent preferably comprises a polymer containing the aforementioned structure. In addition, the self-assembly composition for pattern formation comprises a block copolymer comprising a polymerization unit (a) having at least one selected from the structure represented by the above formula (103) and the structure represented by the above formula (104), and a polymerization unit (b) having the structure represented by the above formula (105), and the content rate of a sugar moiety in the block copolymer is 3% by mass or more and 80% by mass or less, based on the total mass of the block copolymer.

The under coating agent preferably comprises a polymer comprising the aforementioned structure, and the content of the polymer in the under coating agent is preferably 0.1% by mass or more and 99% by mass or less, and more preferably 0.1% by mass or more and 50% by mass or less, based on the total mass of the under coating agent.

The under coating agent may further comprise a solvent. Examples of the solvent include an alcohol solvent, an ether solvent, a ketone solvent, a sulfur-containing solvent, an amide solvent, an ester solvent, and a hydrocarbon solvent.

Moreover, the under coating agent may further comprise, as optional components, an ionic liquid, a surfactant, and the like. By allowing the under coating agent to comprise an ionic liquid, the compatibility of the polymer with the above-described solvent can be enhanced. Furthermore, the phase separation performance of a self-assembly composition for pattern formation to be applied onto the under layer can also be enhanced.

By allowing the under coating agent to comprise a surfactant, the coating properties of the under coating agent applied onto the substrate upon formation of a pattern can be improved. Further, the coating properties of a self-assembly composition for pattern formation and the like, which are to be applied after the under coating agent, can be improved. Examples of a preferred surfactant include a nonionic surfactant, a fluorine-based surfactant, and a silicone-based surfactant.

(Laminate)

The present invention may also relate to a laminate having a substrate, an under layer, and a pattern-forming layer in this order. The under layer is composed of the aforementioned under coating agent, and the under layer comprises a polymer containing at least one selected from a (meth)acrylate-derived unit optionally having a substituent and a styrene-derived unit optionally having a substituent. Moreover, the pattern-forming layer comprises a block copolymer comprising a polymerization unit (a) having at least one selected from the structure represented by the above formula (103) and the structure represented by the above formula (104), and a polymerization unit (b) having the structure represented by the above formula (105), and the content rate of a sugar moiety in the block copolymer is 3% by mass or more and 80% by mass or less, based on the total mass of the block copolymer.

The substrate, the under layer, and the pattern-forming layer are preferably laminated on one another in this order, such that the adjacent layers are directly contacted with each other. However, another layer may be established between individual layers. For instance, an anchoring layer may be established between the substrate and the under layer. The anchoring layer is a layer for controlling the wettability of the substrate, and enhances the adhesiveness between the substrate and the under layer.

Examples

The characteristics of the present invention will be more specifically described in the following examples and comparative examples. The materials, used amounts, ratios, treatment contents, treatment procedures, etc. can be appropriately modified, unless they are deviated from the gist of the present invention. Accordingly, the scope of the present invention should not be restrictively interpreted by the following specific examples.

Synthesis of Polymer 1

Synthesis of Sugar methacrylate 1

33 g of xylose was dissolved in 150 mL of water, and 28.5 g each of ammonium hydrogen carbonate was added to the solution every 24 hours, four times. The obtained mixture was stirred at 37° C. for 96 hours. Thereafter, 200 mL of distilled water was added to the reaction mixture, and water was distilled away to result in a volume of 20 mL. After that, 150 mL of water was added to the reaction mixture, and the obtained mixture was then concentrated to a volume of 10 mL. These operations were carried out repeatedly, until ammonia odor disappeared. The resultant was freeze-dried to obtain a white solid. This substance was examined by FT-IR, and as a result, an NH-derived peak was observed around 1500 cm$^{-1}$. Thus, it was confirmed that the substance could be aminated.

This substance was dissolved in 50 mL of a $1 \times 10^{-3}$ M KOH aqueous solution, and 10.4 g of 2-isocyanate ethyl methacrylate was then added to the solution. The obtained solution was intensively stirred for 12 hours, while the temperature was kept at 3° C. The precipitated white solid was removed, and the filtrate was then washed using 50 mL of diethyl ether four times, followed by performing freeze-drying. Thereafter, the obtained white solid was dissolved in a mixed solution consisting of 2 mL of water and 10 mL of methanol, and the thus obtained solution was then added dropwise to a mixed solution of 200 mL of acetone, followed by cooling. Thereafter, the reaction solution was filtrated through a filter, and was then dried under reduced pressure, to obtain 2-(methacryloyloxy)ethyl ureide xylose.

From the FT-IR spectrum, a peak derived from NH—CO—NH mutual stretching was found at 1570 cm$^{-1}$, a peak derived from C=O (urea) stretching vibration was found at 1650 cm$^{-1}$, and a peak derived from C=O (ester) stretching vibration was found at 1705 cm$^{-1}$. Thus, it was confirmed that sugar methacrylate 1 could be synthesized.

Synthesis of acetyl Sugar methacrylate 1

The above-synthesized sugar methacrylate 1 (10 g) was allowed to react with 120 g of acetic anhydride for 2 hours. Thereafter, the reaction was terminated by addition of a 33% magnesium acetate solution, and pure water was then added to the reaction mixture to precipitate acetyl sugar methacrylate 1.

Synthesis of polystyrene (PS)-acetyl Sugar methacrylate 1 Block Copolymer

To a flask, 500 mL of tetrahydrofuran and 92 g of a THF solution (manufactured by Tokyo Chemical Industry Co., Ltd.) containing 2.6% by mass of lithium chloride were added, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 18.8 g of styrene (manufactured by Wako Pure Chemical Industries, Ltd.) was added to the reaction mixture, and the thus obtained mixture was then stirred for 15 minutes. Thereafter, 1 g of diphenylethylene (manufactured by Wako Pure Chemical Industries, Ltd.) was further added to the reaction mixture, followed by stirring for 5 minutes. Thereafter, 188 g of acetyl sugar methacrylate 1 was added to the reaction mixture, and the thus obtained mixture was further stirred for 15 minutes. After that, 7 g of methanol was added to the reaction mixture to terminate the reaction. The obtained block copolymer was washed, filtrated, and concentrated. The structure of the PS-acetyl sugar methacrylate 1 block copolymer (Polymer 1) is as follows.

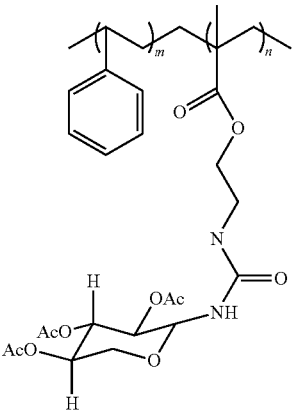

[Formula 46]

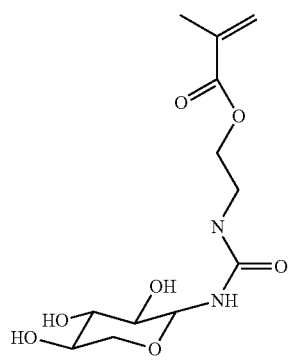

[Formula 45]

wherein m=21 and n=23.

Synthesis of Polymer 2

Synthesis of PS-acetyl Sugar methacrylate 1-ran-methyl methacrylate Block Copolymer Sugar methacrylate 1 was synthesized in the same manner as that of the above <Synthesis of sugar methacrylate 1>, with the exception that xylose was converted to xylooligosaccharide having an average sugar chain length of 3 in the above <Synthesis of sugar methacrylate 1>. Acetyl sugar methacrylate 1 was synthesized in the same manner as that of the above <Synthesis of acetyl sugar methacrylate 1>.

Synthesis of Polystyrene (PS)-acetyl Sugar methacrylate 1-ran-methyl methacrylate Block Copolymer To a flask, 1000 mL of tetrahydrofuran and 92 g of a THF solution (manufactured by Tokyo Chemical Industry Co., Ltd.) containing 2.6% by mass of lithium chloride were added, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 48 g of styrene (manufactured by Wako Pure Chemical Industries, Ltd.) was added to the reaction mixture, and the thus obtained mixture was then stirred for 1 hour. Thereafter, 1 g of diphenylethylene was further added to the reaction mixture, followed by stirring for 5 minutes. Thereafter, a mixture consisting of 90 g of acetyl sugar methacrylate 1 and 25 g of methyl methacrylate (manufactured by Wako Pure Chemical Industries, Ltd.) was added to the reaction mixture, and the thus obtained mixture was further stirred for 30 minutes. After that, 14 g of methanol was added to the reaction mixture to terminate the reaction. The obtained block copolymer was washed, filtrated, and concentrated. The structure of the PS-acetyl sugar methacrylate 1-ran-methyl methacrylate block copolymer (Polymer 2) is as follows.

[Formula 47]

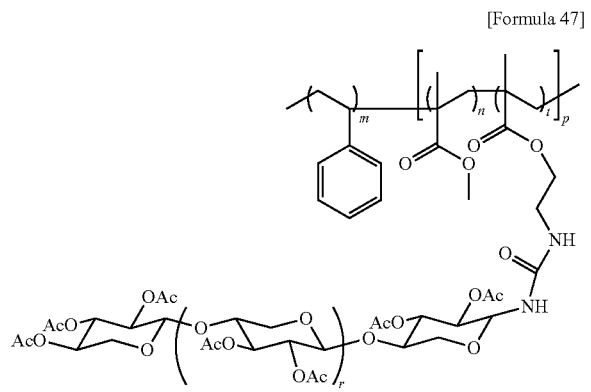

wherein m=1310, n=505, l=56, p=1, and r=1.

Synthesis of Polymer 3

Synthesis of acetyl Sugar Styrene

Acetyl sugar was synthesized in the same manner as that of the above <Synthesis of acetyl sugar methacrylate 1>, with the exception that xylooligosaccharide having an average polymerization degree of 3 was used instead of sugar methacrylate 1 in the above <Synthesis of acetyl sugar methacrylate 1>. Subsequently, 10.8 g (90 mmol) of 4-vinylphenol, 32.2 g (32 mmol) of acetyl sugar, and 0.5 g of zinc chloride were heated in a silicon oil bath at 160° C. for 30 minutes, while stirring. The molten mixture was cooled to approximately 60° C., and was then dissolved in 200 mL of benzene. The obtained solution was washed with water twice, and was then washed with 1 M sodium hydroxide, until the water phase became almost colorless, and was further washed with water twice. Thereafter, the resultant was dried, and was then concentrated under reduced pressure to obtain 26.5 g of acetyl sugar styrene.

Synthesis of polytrimethylsilylstyrene (PTMSS)-acetyl Sugar Styrene Block Copolymer To a flask, 1000 mL of tetrahydrofuran and 92 g of a THF solution (manufactured by Tokyo Chemical Industry Co., Ltd.) containing 2.6% by mass of lithium chloride were added, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 40 g of trimethylsilylstyrene (manufactured by Schiller Laboratories) was added to the reaction mixture, and the obtained mixture was then stirred for 50 minutes. Then, 1 g of diphenylethylene was added to the reaction mixture, and the obtained mixture was then stirred for 5 minutes. Thereafter, 110 g of acetyl sugar styrene was added to the reaction mixture, and the thus obtained mixture was further stirred for 20 minutes. After that, 15 g of methanol was added to the reaction mixture to terminate the reaction. The obtained block copolymer was washed, filtrated, and concentrated. The structure of the PTMSS-acetyl sugar styrene block copolymer (Polymer 3) is as follows.

[Formula 48]

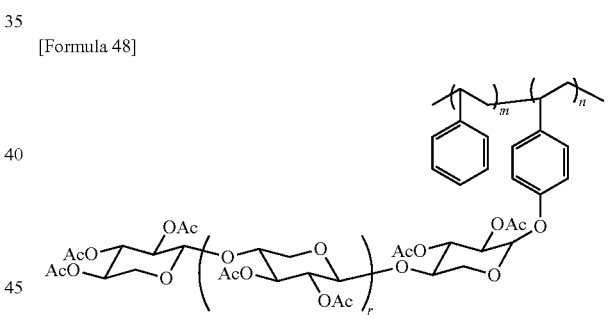

wherein m=286, n=123, and r=1.

Synthesis of Polymer 4

Synthesis of acetyl Sugar methacrylate 2

10 g of xylose was added to a mixed solution of 120 g of acetic anhydride and 160 g of acetic acid, and the obtained solution was then stirred at 30° C. for 2 hours. Approximately five times amount of cold water was slowly added to the reaction solution, while stirring, and the obtained mixture was then stirred for 2 hours. Thereafter, the reaction mixture was left at rest overnight. The precipitated crystal (10 g) was added to a solution prepared by adding 0.6 g of ethylenediamine and 0.7 g of acetic acid to 200 mL of THF in a flask and setting the temperature at 0° C., and the obtained mixture was then stirred for 4 hours. This reaction mixture was poured into 500 mL of cold water, and was then extracted with dichloromethane twice. The obtained extract (10 g), 150 mL of dichloromethane and 2.4 g of triethylamine were added into a flask, and were then cooled to −30° C. Thereafter, 1.4 g of methacryloyl chloride was added to the reaction mixture, and the thus obtained mixture was then stirred for 2 hours. The obtained reaction mixture was poured into 150 mL of cold water, and was the extracted with dichloromethane twice, and the solvent was then concentrated to obtain 8.1 g of acetyl sugar methacrylate 2.

Synthesis of PS-acetyl Sugar methacrylate 2 Block Copolymer 500 mL of Tetrahydrofuran and 92 g of a THF solution (manufactured by Tokyo Chemical Industry Co., Ltd.) containing 2.6% by mass of lithium chloride were added into a flask, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 18.8 g of styrene (manufactured by Wako Pure Chemical Industries, Ltd.) was added to the reaction mixture, and the thus obtained mixture was then stirred for 15 minutes. Thereafter, 1 g of diphenylethylene (manufactured by Wako Pure Chemical Industries, Ltd.) was further added to the reaction mixture, followed by stirring for 5 minutes. Thereafter, 188 g of acetyl sugar methacrylate 2 was added to the reaction mixture, and the thus obtained mixture was further stirred for 15 minutes. After that, 7 g of methanol was added to the reaction mixture to terminate the reaction. The obtained block copolymer was washed, filtrated, and concentrated. The structure of the PS-acetyl sugar methacrylate 2 block copolymer (Polymer 4) is as follows.

[Formula 49]

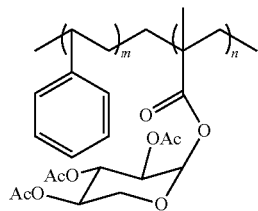

wherein m=51 and n=53.

Synthesis of Polymer 5

Synthesis of PS-acetyl Sugar methacrylate 2-ran-methyl methacrylate Block Copolymer Acetyl sugar methacrylate 2 was synthesized in the same manner as that of the above <Synthesis of acetyl sugar methacrylate 2>, with the exception that xylose was converted to xylooligosaccharide (average sugar chain length: 3) in the above <Synthesis of acetyl sugar methacrylate 2>.

Synthesis of PS-acetyl Sugar methacrylate 2-ran-methyl methacrylate Block Copolymer To a flask, 1000 mL of tetrahydrofuran and 92 g of a THF solution (manufactured by Tokyo Chemical Industry Co., Ltd.) containing 2.6% by mass of lithium chloride were added, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 48 g of styrene (manufactured by Wako Pure Chemical Industries, Ltd.) was added to the reaction mixture, and the thus obtained mixture was then stirred for 1 hour. Thereafter, 1 g of diphenylethylene was further added to the reaction mixture, followed by stirring for 5 minutes. Thereafter, a mixture consisting of 90 g of acetyl sugar methacrylate 2 and 25 g of methyl methacrylate (manufactured by Wako Pure Chemical Industries, Ltd.) was added to the reaction mixture, and the thus obtained mixture was further stirred for 30 minutes. After that, 14 g of methanol was added to the reaction mixture to terminate the reaction. The obtained block copolymer was washed, filtrated, and concentrated. The structure of the PS-acetyl sugar methacrylate 2-ran-methyl methacrylate block copolymer (Polymer 5) is as follows.

[Formula 50]

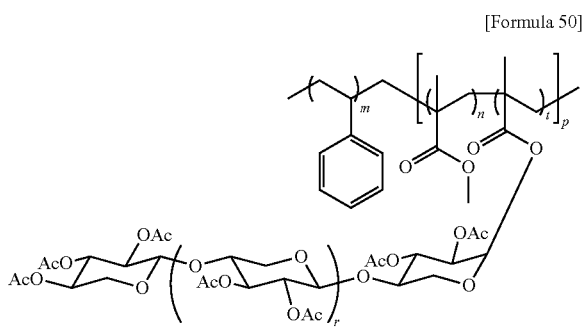

wherein m=788, n=169, l=169, p=1, and r=1.

Synthesis of Polymer 6

Synthesis of PS-methyl methacrylate Block Copolymer

To a flask, 1000 mL of tetrahydrofuran and 92 g of a THF solution (manufactured by Tokyo Chemical Industry Co., Ltd.) containing 2.6% by mass of lithium chloride were added, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 48 g of styrene was added to the reaction mixture, and the thus obtained mixture was then stirred for 1 hour. Thereafter, 1 g of diphenylethylene was further added to the reaction mixture, followed by stirring for 5 minutes. Thereafter, 70 g of methyl methacrylate (manufactured by Wako Pure Chemical Industries, Ltd.) was added to the reaction mixture, and the thus obtained mixture was further stirred for 30 minutes. After that, 14 g of methanol was added to the reaction mixture to terminate the reaction. The obtained block copolymer was washed, filtrated, and concentrated, so as to obtain 55 g of a PS-methyl methacrylate block copolymer (Polymer 6). The structure of the PS-methyl methacrylate block copolymer (Polymer 6) is as follows.

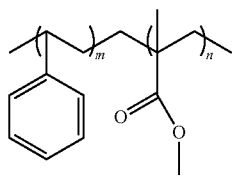

wherein m=1566 and n=671.

Synthesis of Polymer 7

Synthesis of PTMSS-hydroxystyrene Block Copolymer

To a flask, 1000 mL of tetrahydrofuran and 92 g of a THF solution (manufactured by Tokyo Chemical Industry Co., Ltd.) containing 2.6% by mass of lithium chloride were added, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 48 g of trimethylsilylstyrene was added to the reaction mixture, and the thus obtained mixture was then stirred for 1 hour. Thereafter, 1 g of diphenylethylene (manufactured by BOC Sciences) was further added to the reaction mixture, followed by stirring for 5 minutes. Thereafter, 70 g of 4-(t-butyldimethylsiloxy)styrene was added to the reaction mixture, and the thus obtained mixture was further stirred for 30 minutes. After that, 14 g of methanol was added to the reaction mixture to terminate the reaction. The obtained block copolymer was filtrated, was then concentrated and was then allowed to react with 2 N hydrochloric acid in THF, so as to obtain a PTMSS-hydroxystyrene block copolymer (Polymer 7). The structure of the PTMSS-hydroxystyrene block copolymer (Polymer 7) is as follows.

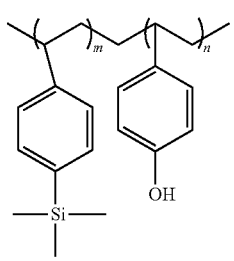

wherein m=660 and n=283.

Synthesis of Polymer 8

Polymer 8 was synthesized in the same manner as that of the above (Synthesis of Polymer 5), with the exception that the molar ratio of styrene:acetyl sugar methacrylate 2:methyl methacrylate was set at 3:1:6 in the above (Synthesis of Polymer 5).

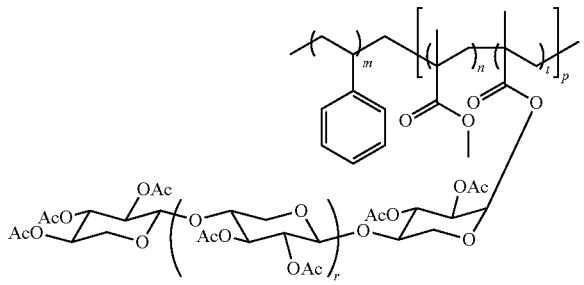

wherein m=401, n=794, l=140, p=1, and r=1.

Analysis

Molecular Weight

The weight average molecular weight of a block copolymer was measured by a gel permeation chromatography (GPC) method.
GPC column: Shodex K-806M/K-802 coupled column (manufactured by SHOWA DENKO K. K.)
Column temperature: 40° C.
Mobile phase: chloroform
Detector: RI When a block copolymer was synthesized, a first block (polymerization unit (a)) was initially polymerized. Thereafter, a portion was removed from the first block, and the polymerization degree thereof was then confirmed by the GPC method. Thereafter, a second block (polymerization unit (b)) was polymerized, and the polymerization degree thereof was then confirmed also by the GPC method, so that it was confirmed that a block copolymer having a desired polymerization degree and a desired average molecular weight could be synthesized. PDI indicates weight average molecular weight Mw/number average molecular weight Mn.

<Hydrophobic Portion/Hydrophilic Portion (Unit) Ratio>

The unit ratio of a block copolymer was calculated by obtaining the ratio (molar ratio) between the polymerization unit (a) and the polymerization unit (b) according to $^1$H-NMR.

<Content Rate of Sugar Moiety>

The content rate of the sugar moiety was obtained according the following equation:

Content rate of sugar moiety (% by mass)=polymerization degree of sugar-derived unit(s)×molecular weight of sugar×number of units with polymerization degree (a)/weight average molecular weight of block copolymer Herein, the number of units with the polymerization degree (a) was calculated from the weight average molecular weight of the block copolymer, the unit ratio, and the molecular weight of each structural unit.

TABLE 1

|  | Hydrophobic portion | Hydrophilic portion | Molecular weight | PDI | Hydrophobic portion:hydrophilic portion (molar ratio) | Sugar moiety content rate (mass %) |
|---|---|---|---|---|---|---|
| Polymer 1 | Styrene | Acetyl sugar methacrylate 1 | 20,000 | 1.12 | 48:52 | 49 |
| Polymer 2 | Styrene | Acetyl sugar methacrylate 1-ran-methyl methacrylate | 230,000 | 1.2 | 70:30 | 17 |
| Polymer 3 | Trimethylsilylstyrene | Acetyl sugar styrene | 150,000 | 1.2 | 70:30 | 57 |
| Polymer 4 | Styrene | Acetyl sugar methacrylate 2 | 20,000 | 1.12 | 49:51 | 55 |
| Polymer 5 | Styrene | Acetyl sugar methacrylate 2-ran-methyl methacrylate | 230,000 | 1.2 | 70:30 | 51 |
| Polymer 6 | Styrene | Methyl methacrylate | 230,000 | 1.2 | 70:30 | 0 |
| Polymer 7 | Trimethylsilylstyrene | Hydroxystyrene | 150,000 | 1.1 | 70:30 | 0 |
| Polymer 8 | Styrene | Acetyl sugar methacrylate 2-ran-methyl methacrylate | 230,000 | 1.1 | 30:70 | 42 |

Synthesis of Under Coating Agent 1

500 mL of Tetrahydrofuran and 92 g of a THF solution (manufactured by Tokyo Chemical Industry Co., Ltd.) containing 2.6% by mass of lithium chloride were added into a flask, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 30 g of styrene and 30 g of methyl methacrylate were added to the reaction mixture, and the thus obtained mixture was then stirred for 30 minutes. Thereafter, 7 g of methanol was added to the reaction mixture to terminate the reaction. The structure of a polymer contained in the obtained under coating agent 1 is as follows.

[Formula 54]

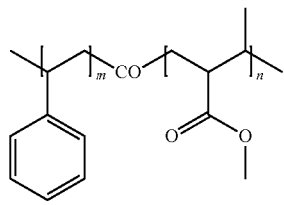

wherein m=244 and n=286.

Synthesis of Under Coating Agent 2

500 mL of Tetrahydrofuran and 92 g of a THF solution (manufactured by Tokyo Chemical Industry Co., Ltd.) containing 2.6% by mass of lithium chloride were added into a flask, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 30 g of styrene, 50 g of acetyl sugar methacrylate, and 30 g of methyl methacrylate were added to the reaction mixture, and the thus obtained mixture was then stirred for 30 minutes. Thereafter, 7 g of methanol was added to the reaction mixture to terminate the reaction, thereby obtaining an under coating agent 2. The structure of a polymer contained in the obtained under coating agent 2 is as follows.

[Formula 55]

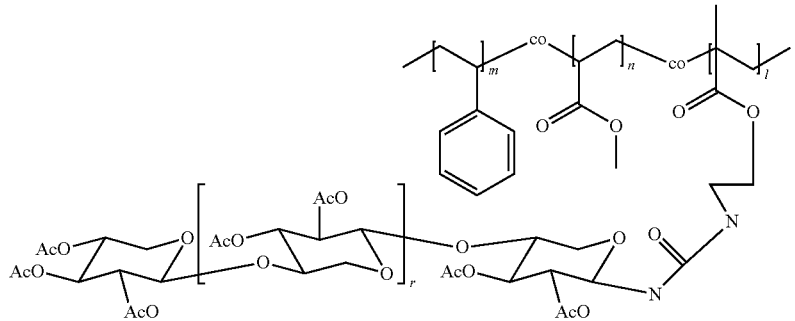

wherein m=153, n=157, l=23, and r=1.

Synthesis of Under Coating Agent 3

500 mL of Tetrahydrofuran and 92 g of a THF solution (manufactured by Tokyo Chemical Industry Co., Ltd.) containing 2.6% by mass of lithium chloride were added into a flask, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 30 g of styrene and 270 g of acetyl sugar methacrylate 1 were added to the reaction mixture, and the thus obtained mixture was then stirred for 30 minutes. Thereafter, 7 g of methanol was added to the reaction mixture to terminate the reaction, thereby obtaining an under coating agent 3. The structure of a polymer contained in the obtained under coating agent 3 is as follows.

wherein m=32, n=48, and r=2.

Synthesis of Under Coating Agent 4

500 mL of Tetrahydrofuran and 92 g of a THF solution (manufactured by Tokyo Chemical Industry Co., Ltd.) containing 2.6% by mass of lithium chloride were added into a flask, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 30 g of styrene and 180 g of acetyl sugar methacrylate 2 were added to the reaction mixture, and the thus obtained mixture was then stirred for 30 minutes. Thereafter, 7 g of methanol was added to the

[Formula 56]

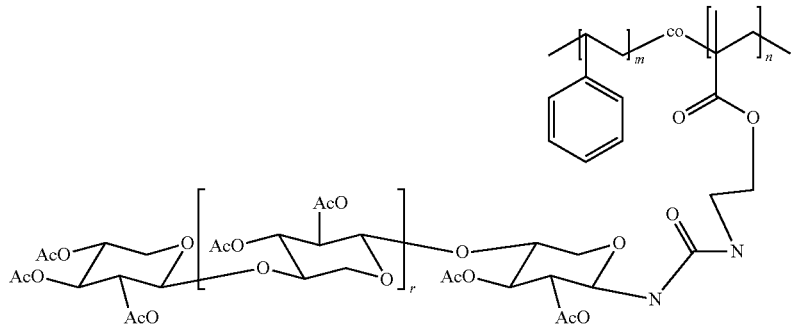

reaction mixture to terminate the reaction, thereby obtaining an under coating agent 4. The structure of a polymer contained in the obtained under coating agent 4 is as follows.

[Formula 57]

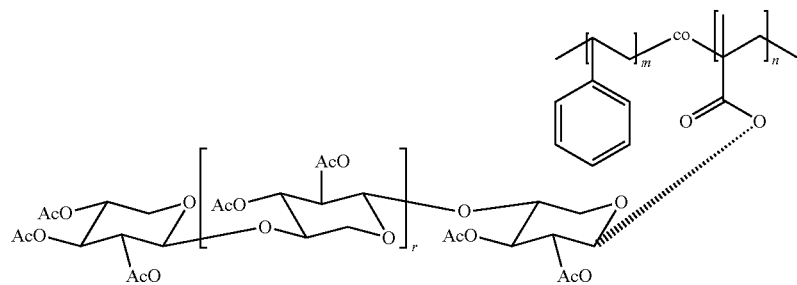

wherein m=124, n=53, and r=1.

Synthesis of Under Coating Agent 5

500 mL of Tetrahydrofuran and 92 g of a THF solution (manufactured by Tokyo Chemical Industry Co., Ltd.) containing 2.6% by mass of lithium chloride were added into a flask, and the obtained mixture was then cooled to −78C in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/de-aeration treatment. Subsequently, 30 g of trimethylsilylstyrene and 40 g of 4-(t-butyldimethylsiloxy)styrene were added to the reaction mixture, and the thus obtained mixture was further stirred for 30 minutes. Thereafter, 14 g of methanol was added to the reaction mixture to terminate the reaction. The obtained block copolymer was filtrated, was then concentrated and was then allowed to react with 2 N hydrochloric acid in THF, so as to obtain an under coating agent 5. The structure of a polymer contained in the obtained under coating agent 5 is as follows.

[Formula 58]

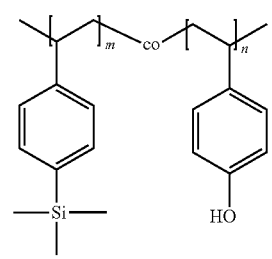

wherein m=101 and n=101.

Synthesis of Under Coating Agent 6

500 mL of Tetrahydrofuran and 92 g of a THF solution (manufactured by Tokyo Chemical Industry Co., Ltd.) containing 2.6% by mass of lithium chloride were added into a flask, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/ deaeration treatment. Subsequently, 30 g of trimethylsilylstyrene, 35 g of 4-(t-butyldimethylsiloxy)styrene, and 80 g of acetyl sugar styrene were added to the reaction mixture, and the thus obtained mixture was further stirred for 30 minutes. Thereafter, 14 g of methanol was added to the reaction mixture to terminate the reaction. The obtained block copolymer was filtrated, was then concentrated and was then allowed to react with 2 N hydrochloric acid in THF, so as to obtain an under coating agent 6. The structure of a polymer contained in the obtained under coating agent 6 is as follows.

[Formula 59]

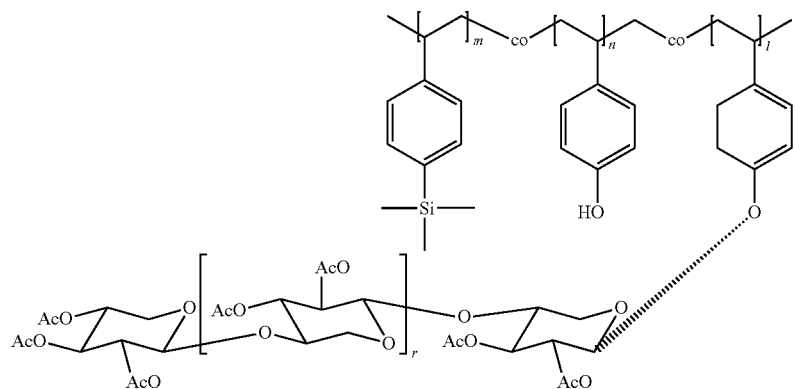

wherein m=81, n=71, l=17, and r=2.

Synthesis of Under Coating Agent 7

An under coating agent 7 was obtained in the same manner as that of the above (Synthesis of under coating agent 1), with the exceptions that the molar ratio between styrene and methyl methacrylate was set at 1:9 and the reaction time was adjusted to result in a molecular weight of 10,000 in the above (Synthesis of under coating agent 1).

[Formula 60]

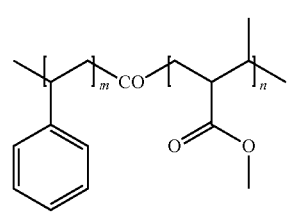

wherein m=10 and n=90.

Synthesis of Under Coating Agent 8

500 mL of Tetrahydrofuran and 92 g of a THF solution (manufactured by Tokyo Chemical Industry Co., Ltd.) containing 2.6% by mass of lithium chloride were added into a flask, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 7 g of styrene, 50 g of acetyl sugar methacrylate 2, and 50 g of methyl methacrylate were added to the reaction mixture, and the thus obtained mixture was then stirred for 15 minutes. Thereafter, 7 g of methanol was added to the reaction mixture to terminate the reaction, thereby obtaining an under coating agent 8.

[Formula 61]

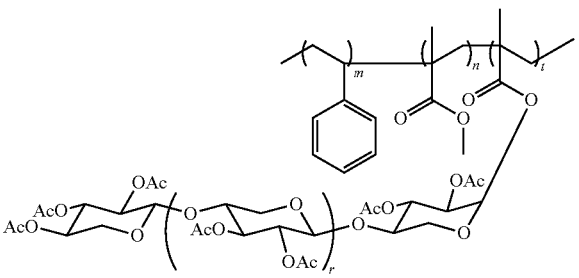

wherein m=7, n=57, l=7, and r=1.

TABLE 2

| | Component 1 | Hydrophilic portion 1 | Hydrophilic portion 2 | Molecular weight | PDI | Hydrophobic portion:hydrophilic portion 1:hydrophilic portion 2 (molar ratio) |
|---|---|---|---|---|---|---|
| Under coating agent 1 | Styrene | Methyl methacrylate | — | 54,000 | 1.5 | 46:54:0 |
| Under coating agent 2 | Styrene | Acetyl sugar methacrylate 1 | Methyl methacrylate | 55,000 | 1.7 | 46:7:47 |
| Under coating agent 3 | Styrene | Acetyl sugar methacrylate 1 | — | 55,000 | 1.5 | 40:60:0 |
| Under coating agent 4 | Styrene | Acetyl sugar methacrylate 2 | — | 54,000 | 1.6 | 70:30:00 |
| Under coating agent 5 | Trimethylsilylstyrene | p-Hydroxystyrene | — | 30,000 | 1.15 | 50:50:0 |
| Under coating agent 6 | Trimethylsilylstyrene | Acetyl sugar styrene | p-Hydroxystyrene | 40,000 | 1.2 | 48:10:42 |
| Under coating agent 7 | Styrene | Methyl methacrylate | — | 10,000 | 2 | 10:90 |
| Under coating agent 8 | Styrene | Acetyl sugar methacrylate 2 | Methyl methacrylate | 12,000 | 1.7 | 10:80:10 |

Examples 1 to 7 and Comparative Examples 1 and 2

Polymers 1 to 7 (self-assembly compositions for pattern formation) were each dissolved in PGMEA to result in a concentration of 1% by mass, and the obtained solutions were each filtrated using a 0.2 μm filter. Under coating agents 1 to 6 were each dissolved in PGMEA to result in a concentration of 1% by mass, and the obtained solutions were each filtrated using a 0.2 μm filter. Using a spin coater, a PGMEA solution comprising 1% by mass of an under coating agent was applied onto a silicon wafer with a size of 3 inches to result in a thickness of 20 nm, and a heat treatment was then performed on a hot plate at 230° C. for 5 minutes. Subsequently, using a spin coater, a PGMEA solution comprising 1% by mass of a polymer (a self-assembly composition for pattern formation) was applied to the surface of the silicon wafer, on which the under coating agent had been applied, to result in a thickness of 25 nm, and a heat treatment was then performed on a hot plate at 230° C. for 5 minutes. Using an ICP plasma etching apparatus (manufactured by Tokyo Electron, Ltd.), the substrate was subjected to an oxygen plasma treatment (100 sccm, 4 Pa, 100 W, and 20 sec), so that a hydrophilic portion was selectively removed.

Evaluation

<Vertical Orientation>
The vertical orientation state was evaluated in accordance with the following evaluation criteria.
◦: A state in which a pattern is vertically oriented in one visual field of SEM (in the case of vertical cylinder or lamellar, a finger print pattern can be regularly observed).
x: A state in which a pattern is partially horizontally oriented (a state in which the regularity of a pattern is collapsed).
<Shape>
The surface of a self-assembly layer was observed by SEM, and a phase-separated structure was observed. Using a scanning electron microscope JSM 7800F (manufactured by JEOL), the surface was observed at an accelerating voltage of 1.5 kV, at an emission current of 37.0 µA, and at magnification of 100,000-fold.

TABLE 3

| | Under coating agent | Block copolymer | Vertical orientation | Shape |
|---|---|---|---|---|
| Ex. 1 | Under coating agent 1 | Polymer 1 | ◦ | Lamellar |
| Ex. 2 | Under coating agent 2 | Polymer 2 | ◦ | Cylinder |
| Ex. 3 | Under coating agent 3 | Polymer 2 | ◦ | Cylinder |
| Ex. 4 | Under coating agent 5 | Polymer 3 | ◦ | Cylinder |
| Ex. 5 | Under coating agent 6 | Polymer 3 | ◦ | Cylinder |
| Ex. 6 | Under coating agent 1 | Polymer 4 | ◦ | Lamellar |
| Ex. 7 | Under coating agent 4 | Polymer 5 | ◦ | Cylinder |
| Ex. 8 | Under coating agent 7 | Polymer 8 | ◦ | Cylinder |
| Ex. 9 | Under coating agent 8 | Polymer 8 | ◦ | Cylinder |
| Comp. Ex. 1 | Under coating agent 1 | Polymer 6 | x | Undeterminable |
| Comp. Ex. 2 | Under coating agent 5 | Polymer 7 | x | Undeterminable |

As is found from Table 3, in the Examples, good vertical orientation was achieved, and a desired phase-separated structure could be formed.

At the same time, using Polymers 1 to 3, a phase-separated structure was formed without forming an under layer. As a result, vertical orientation was not favorable in some cases, and the error rate of pattern position was slightly increased.

REFERENCE SIGNS LIST

1 SELF-ASSEMBLY COMPOSITION FOR PATTERN FORMATION
10 BLOCK COPOLYMER
50 GUIDE HOLE
55 HOLE PART
60 GUIDE PATTERN
62 POST GUIDE
70 SUBSTRATE
80 UNDER LAYER
P PHASE
Q PHASE

The invention claimed is:
1. A pattern forming method comprising:
applying an under coating agent onto a substrate, and
applying a self-assembly composition for pattern formation to the surface of the substrate, onto which the under coating agent has been applied, and then forming a self-assembly film according to self-assembly phase separation, wherein
the self-assembly composition for pattern formation comprises a block copolymer comprising a polymerization unit (a) having at least one selected from a structure represented by the following formula (103) and a structure represented by the following formula (104), and a polymerization unit (b) having a structure represented by the following formula (105), and
the content rate of a sugar moiety in the block copolymer is 3% by mass or more and 80% by mass or less, based on the total mass of the block copolymer:

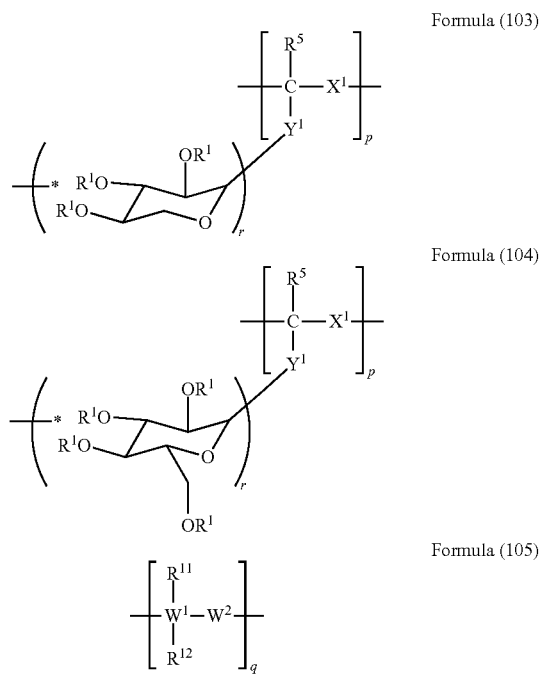

wherein, in the formulae (103) and (104), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ is identical to or different from one another; $R^5$ represents a hydrogen atom or an alkyl group, and a plurality of $R^5$ is identical to or different from one another; $X^1$ and $Y^1$ each independently represent a single bond or a linking group, a plurality of $X^1$ is identical to or different from one another, and a plurality of $Y^1$ is identical to or different from one another; p represents an integer of 2 or more and 3000 or less, r represents an integer of 0 or more, and at least one of a plurality of r represents an integer of 1 or more; and the symbol * represents a binding site with any one of $R^1$, or a binding site with any one oxygen atom to which $R^1$ binds, instead of $R^1$, when r represents 2 or more; and
in the formula (105), $W^1$ represents a carbon atom or a silicon atom, and a plurality of $W^1$ is identical to or different from one another; $W^2$ represents —$CR_2$—, —O—, —S—, or —$SiR_2$— (provided that R represents a hydrogen atom or an alkyl group containing 1 to 5 carbon atoms, and a plurality of R is identical to or different from one another), and a plurality of $W^2$ is identical to or different from one another; $R^{11}$ represents a hydrogen atom, a methyl group, or a hydroxyl group, and a plurality of $R^{11}$ is identical to or different from one another; $R^{12}$ represents a hydrogen atom, a hydroxyl group, an acetyl group, a methoxycarbonyl group, an aryl group, or a pyridyl group, and a plurality of $R^{12}$ is identical to or different from one another; and q represents an integer of 2 or more and 3000 or less.

2. The pattern forming method according to claim 1, wherein the under coating agent comprises a polymer containing at least one selected from a (meth)acrylate-derived unit optionally having a substituent and a styrene-derived unit optionally having a substituent.

3. The pattern forming method according to claim 1, wherein the under coating agent comprises a polymer containing at least one selected from structures represented by the following formulae (203) to (206):

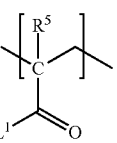
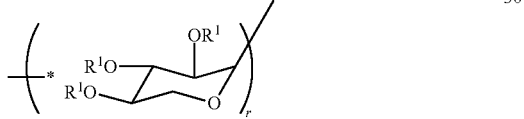

Formula (203)

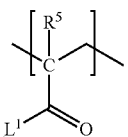
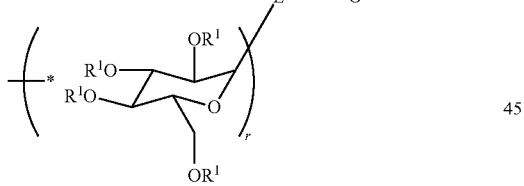

Formula (204)

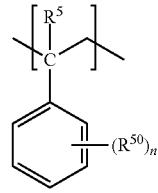

Formula (205)

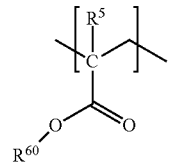

Formula (206)

wherein, in the formulae (203) and (204), $L^1$ represents —O—, —S—, —NH—, —O—$(CH_2)_n$—O—, or —O—$(CH_2)_n$—N—(C=O)—N—, provided that n represents an integer of 1 or more and 10 or less; $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ is identical to or different from one another; $R^5$ represents a hydrogen atom or an alkyl group; r represents an integer of 1 or more, and the symbol * represents a binding site with any one of $R^1$, or a binding site with any one oxygen atom to which $R^1$ binds, instead of $R^1$, when r represents 2 or more;

in the formula (205), $R^5$ represents a hydrogen atom or an alkyl group, $R^{50}$ represents an organic group or a hydroxyl group, and n represents an integer of 0 to 5; and in the formula (206), $R^5$ represents a hydrogen atom or an alkyl group, and $R^{60}$ represents an alkyl group.

4. The pattern forming method according to any claim 1, which further comprises an etching step, after completion of the forming the self-assembly film.

5. The pattern forming method according to claim 4, wherein the etching step is a dry etching step.

6. The pattern forming method according to claim 4, wherein the etching step is a wet etching step.

* * * * *